(12) United States Patent
Nadler et al.

(10) Patent No.: US 11,853,855 B2
(45) Date of Patent: Dec. 26, 2023

(54) MACHINE LEARNING DETECTION AND CLASSIFICATION OF MAXILLOFACIAL BONE LESIONS IN CBCT

(71) Applicants: HADASIT MEDICAL RESEARCH SERVICES & DEVELOPMENT LTD., Jerusalem (IL); JERUSALEM COLLEGE OF TECHNOLOGY, Jerusalem (IL)

(72) Inventors: Chen Nadler, Jerusalem (IL); Ragda Abdalla Aslan, Jerusalem (IL); Talia Yeshua, Jerusalem (IL); Itzhak Leichter, Jerusalem (IL)

(73) Assignees: HADASIT MEDICAL RESEARCH SERVICES & DEVELOPMENT LTD., Jerusalem (IL); JERUSALEM COLLEGE OF TECHNOLOGY, Jerusalem (IL)

( * ) Notice: Subject to any disclaimer, the term of this patent is extended or adjusted under 35 U.S.C. 154(b) by 0 days.

(21) Appl. No.: 18/312,260

(22) Filed: May 4, 2023

(65) Prior Publication Data
US 2023/0359936 A1    Nov. 9, 2023

Related U.S. Application Data

(60) Provisional application No. 63/395,064, filed on Aug. 4, 2022, provisional application No. 63/338,745, filed on May 5, 2022.

(51) Int. Cl.
*G06N 20/00*    (2019.01)

(52) U.S. Cl.
CPC .................................. *G06N 20/00* (2019.01)

(58) Field of Classification Search
CPC ..................................................... G06N 20/00
See application file for complete search history.

(56) References Cited

U.S. PATENT DOCUMENTS

2019/0313963 A1* 10/2019 Hillen .................. G06V 10/764
2020/0305808 A1* 10/2020 Ezhov .................. A61B 6/4085

OTHER PUBLICATIONS

Heo M-S. et al, "Artificial intelligence in oral and maxillofacial radiology: what is currently possible?"; Dentomaxillofac Radiol. vol. 50(3), Mar. 1, 2021.

(Continued)

*Primary Examiner* — John W Lee
(74) *Attorney, Agent, or Firm* — The Roy Gross Law Firm, LLC; Roy Gross

(57) ABSTRACT

A computer-implemented method comprising: receiving a plurality of CBCT scans, each comprising a series of axial slices, wherein the CBCT scans are associated with a cohort of subjects comprising a first subgroup of subjects having each one or more maxillofacial bone lesions, and a second subgroup of subjects having no maxillofacial bone lesions; applying a feature extraction operation to extract a set of features from the axial slices in each of the CBCT scans; at a training stage, training a machine learning model on a training dataset comprising: (i) all of the extracted sets of features, and (ii) annotations indicating boundaries of bone lesions in the axial slices, to obtain a trained machine learning model configured to detect and segment a bone lesion in an axial slice from a CBCT scan.

20 Claims, 12 Drawing Sheets

(56) References Cited

OTHER PUBLICATIONS

Morgan P. McBee et al, "Deep Learning in Radiology"; Acad Radiol; vol. 25(11), pp. 1472-1480, Nov. 2018.
Hwang JJ. et al, "An overview of deep learning in the field of dentistry"; Imaging Sci Dent; vol. 49(1), pp. 1-7, Mar. 2019.
Hung K. et al, "The use and performance of artificial intelligence applications in dental and maxillofacial radiology: A systematic review"; Dentomaxillofac Radiol; vol. 49(1), Jan. 2020.
Pierre Lahoud et al, "Artificial Intelligence for Fast and Accurate 3-Dimensional Tooth Segmentation on Cone-beam Computed Tomography"; J Endod; vol. 47(5), pp. 827-835, May 2021.
Chen Y. et al, "Automatic Segmentation of Individual Tooth in Dental CBCT Images from Tooth Surface Map by a Multi-Task FCN"; IEEE Access; pp. 99:1-1, Jan. 2020.
Tae Jun Jang et al, "A fully automated method for 3D individual tooth identification and segmentation in dental CBCT"; IEEE Transactions on Pattern Analysis and Machine Intelligence; vol. 44, No. 10, pp. 6562-6568, Oct. 1, 2022.
E Yilmaz et al, "Computer-aided diagnosis of periapical cyst and keratocystic odontogenic tumor on cone beam computed tomography"; Comput Methods Programs Biomed; vol. 146, pp. 91-100, Jul. 2017.
"Non-invasive differential diagnosis of dental periapical lesions in cone-beam CT scans"; Med Phys; vol. 42(4), pp. 1653-1665, Apr. 2015.
"Diagnosis of cystic lesions using panoramic and cone beam computed tomographic images based on deep learning neural network"; Oral Dis; vol. 26(1), pp. 152-158, Jan. 2020.
Frank C. Setzer et al, "Artificial Intelligence for the Computer-aided Detection of Periapical Lesions in Cone-beam Computed Tomographic Images"; J Endod, vol. 46(7), pp. 987-993, Jul. 2020.
Jiayu Huang et al, "Combining anatomical constraints and deep learning for 3-D CBCT dental image multi-label segmentation"; IEEE 37th International Conference on Data Engineering; Apr. 19-22, 2021.
K Orhan et al, "Evaluation of artificial intelligence for detecting periapical pathosis on cone-beam computed tomography scans"; Int Endod J; vol. 53(5), pp. 680-689, May 2020.
Fatemeh Abdolali et al, "Automatic segmentation of maxillofacial cysts in cone beam CT images"; Comput Biol Med; vol. 1;72, pp. 108-119, May 2016.
Fatemeh Abdolali et al, "Automated classification of maxillofacial cysts in cone beam CT images using contourlet transformation and Spherical Harmonics"; Comput Methods Programs Biomed; vol. 139, pp. 197-207, Feb. 2017.
Lin, TY. et al. (2014). Microsoft COCO: Common Objects in Context. In: Fleet, D., Pajdla, T., Schiele, B., Tuytelaars, T. (eds) Computer Vision—ECCV 2014. ECCV 2014. Lecture Notes in Computer Science, vol. 8693. Springer, Cham. https://doi.org/10.1007/978-3-319-10602-1_48.

\* cited by examiner

MACHINE LEARNING DETECTION AND CLASSIFICATION OF MAXILLOFACIAL BONE LESIONS IN CBCT

CROSS-REFERENCE TO RELATED APPLICATIONS

This application claims priority from U.S. Application Ser. No. 63/338,745, filed May 5, 2022, entitled "Deep Learning Algorithm for the Detection and 3D Segmentation of Maxillofacial Bone Lesions in CBCT," and U.S. Application Ser. No. 63/395,064, filed Aug. 4, 2022, entitled "Machine Learning Detection and Classification of Maxillofacial Bone Lesions in CBCT," the contents of both of which are hereby incorporated herein in their entirety by reference.

FIELD OF THE INVENTION

This invention relates to the field of machine learning, and, specifically, machine learning systems and methods for detecting or treating a cancer.

BACKGROUND

Cone Beam Computerized Tomography (CBCT) is a volumetric imaging modality used in the oral and maxillofacial field, for diagnosis and treatment planning of both dental and non-dental pathologies, such as bone lesions (BL). Bone lesions typically consist of cysts, benign and malignant tumors, which may be clinically apparent or may be found incidentally on CBCT scans. Incidental BL on CBCT are reported in different frequencies, and require either immediate intervention or follow-up in up to 45.4% of the cases, with 0.3%-1.4% of the cases suspected to be malignant. Detection of incidental benign BL is important in order to prevent bone expansion, dental malocclusion, and the possible advancement into malignant lesions. Moreover, early detection of bone lesions allows for more conservative treatment with reduced morbidity and mortality.

Automated machine learning-based detection of BL in maxillofacial radiology presents unique challenges. BL may be found in both the upper and lower jaws, assume different sizes and shapes, and have various abnormal densities, which radiographically may be either radiolucent, radiopaque, or mixed. Moreover, the scan parameters for CBCT examinations, using the different available CBCT machines and different protocols, may vary in their voxel size, field of view and the anatomical location within the jaw being scanned.

Accordingly, there is a need for a universal fully-automated machine learning-based model configured to detect and segment various forms of BL in CBCT scans.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in an embodiment, a system comprising at least one hardware processor; and a non-transitory computer-readable storage medium having stored thereon program instructions, the program instructions executable by the at least one hardware processor to: receive a plurality of CBCT scans, each comprising a series of axial slices, wherein the CBCT scans are associated with a cohort of subjects comprising a first subgroup of subjects having each one or more maxillofacial bone lesions, and a second subgroup of subjects having no maxillofacial bone lesions, apply a feature extraction operation to extract a set of features from the axial slices in each of the CBCT scans, at a training stage, train a machine learning model on a training dataset comprising: (i) all of the extracted sets of features, and (ii) annotations indicating boundaries of bone lesions in the axial slices, to obtain a trained machine learning model configured to detect and segment a bone lesion in an axial slice from a CBCT scan.

There is also provided, in an embodiment, a computer-implemented method comprising: receiving a plurality of CBCT scans, each comprising a series of axial slices, wherein the CBCT scans are associated with a cohort of subjects comprising a first subgroup of subjects having each one or more maxillofacial bone lesions, and a second subgroup of subjects having no maxillofacial bone lesions; applying a feature extraction operation to extract a set of features from the axial slices in each of the CBCT scans; at a training stage, training a machine learning model on a training dataset comprising: (i) all of the extracted sets of features, and (ii) annotations indicating boundaries of bone lesions in the axial slices, to obtain a trained machine learning model configured to detect and segment a bone lesion in an axial slice from a CBCT scan.

There is further provided, in an embodiment, a computer program product comprising a non-transitory computer-readable storage medium having program instructions embodied therewith, the program instructions executable by at least one hardware processor to: receive a plurality of CBCT scans, each comprising a series of axial slices, wherein the CBCT scans are associated with a cohort of subjects comprising a first subgroup of subjects having each one or more maxillofacial bone lesions, and a second subgroup of subjects having no maxillofacial bone lesions; apply a feature extraction operation to extract a set of features from the axial slices in each of the CBCT scans; at a training stage, train a machine learning model on a training dataset comprising: (i) all of the extracted sets of features, and (ii) annotations indicating boundaries of bone lesions in the axial slices, to obtain a trained machine learning model configured to detect and segment a bone lesion in an axial slice from a CBCT scan.

In some embodiments, the program instructions are further executable to apply, and the method further comprises applying, at an inference stage, the trained machine learning model to a target CBCT scan associated with a target subject, to detect and segment a bone lesion in axial slices in the target CBCT scan.

In some embodiments, the program instructions are further executable to, and the method further comprises, (i) performing pair-wise analysis with respect to successive pairs of axial slices within the target CBCT scan, to calculate a pixel-wise overlap of the segmentations in each of the successive pairs, wherein the successive pairs may be non-consecutive pairs; (ii) identifying a subgroup comprising a minimum number of successive axial slices in which the pixel-wise overlap exceeds a specified threshold, as representing an actual bone lesion; and (iii) correcting segmentation results in any of the axial slices within the subgroup in which the segmentation is incomplete, based on the segmentations in neighboring axial slices.

In some embodiments, the program instructions are further executable to generate, and the method further comprises generating, a 3D segmentation of the bone lesion from the identified subgroup of axial slices.

In some embodiments, the feature extraction operation employs a feature pyramid network (FPN) configured to extract proportionally-sized feature maps at multiple resolution levels from an input CBCT axial slice.

In some embodiments, the annotations indicating the boundaries of the bone lesions comprise one of the following: (i) an exact outline of the bone lesions, wherein the segmenting comprises an exact outline of the bone lesions, or (iii) a bounding box enclosing the bone lesions, wherein the segmenting comprises a bounding box enclosing the bone lesions.

In some embodiments, the training dataset further comprises annotations indicating a malignancy of the bone lesions, wherein the trained machine learning model is further configured to a predict of a malignancy with respect to the bone lesion in the target axial slice.

In some embodiments, the training dataset further comprises annotations indicating a care prioritization level with respect to the one or more bone lesions, wherein the trained machine learning model is further configured to predict the care prioritization level with respect to the bone lesion in the target axial slice.

In addition to the exemplary aspects and embodiments described above, further aspects and embodiments will become apparent by reference to the figures and by study of the following detailed description.

BRIEF DESCRIPTION OF THE FIGURES

The present invention will be understood and appreciated more comprehensively from the following detailed description taken in conjunction with the appended drawings in which:

Figures 6A, 6B, 6C:
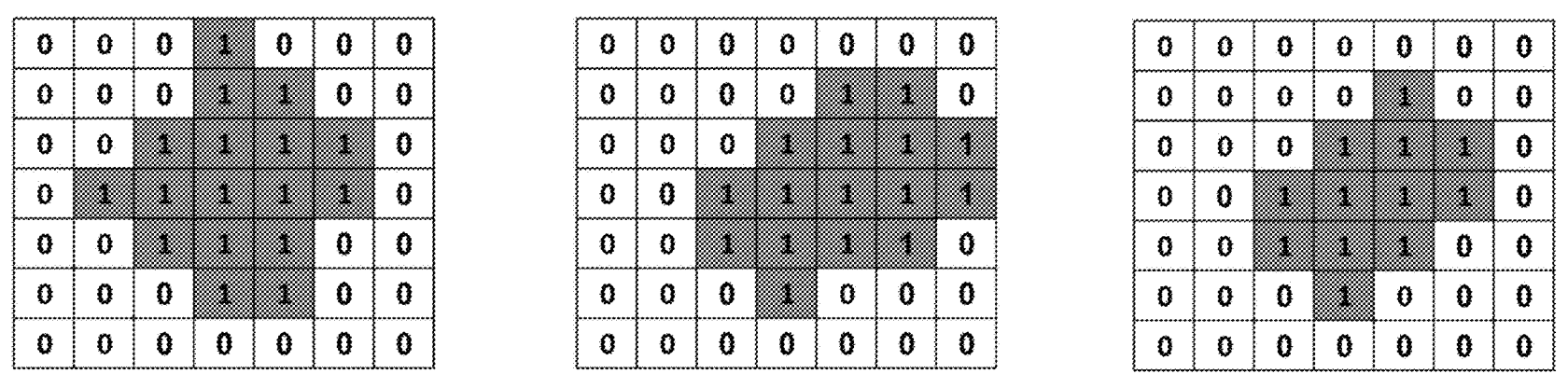

FIGS. 6A-6C and FIG. 7 illustrate a pair-wise axial slices analysis process and results, in accordance with some embodiments of the present invention;

DETAILED DESCRIPTION

Figure 1:
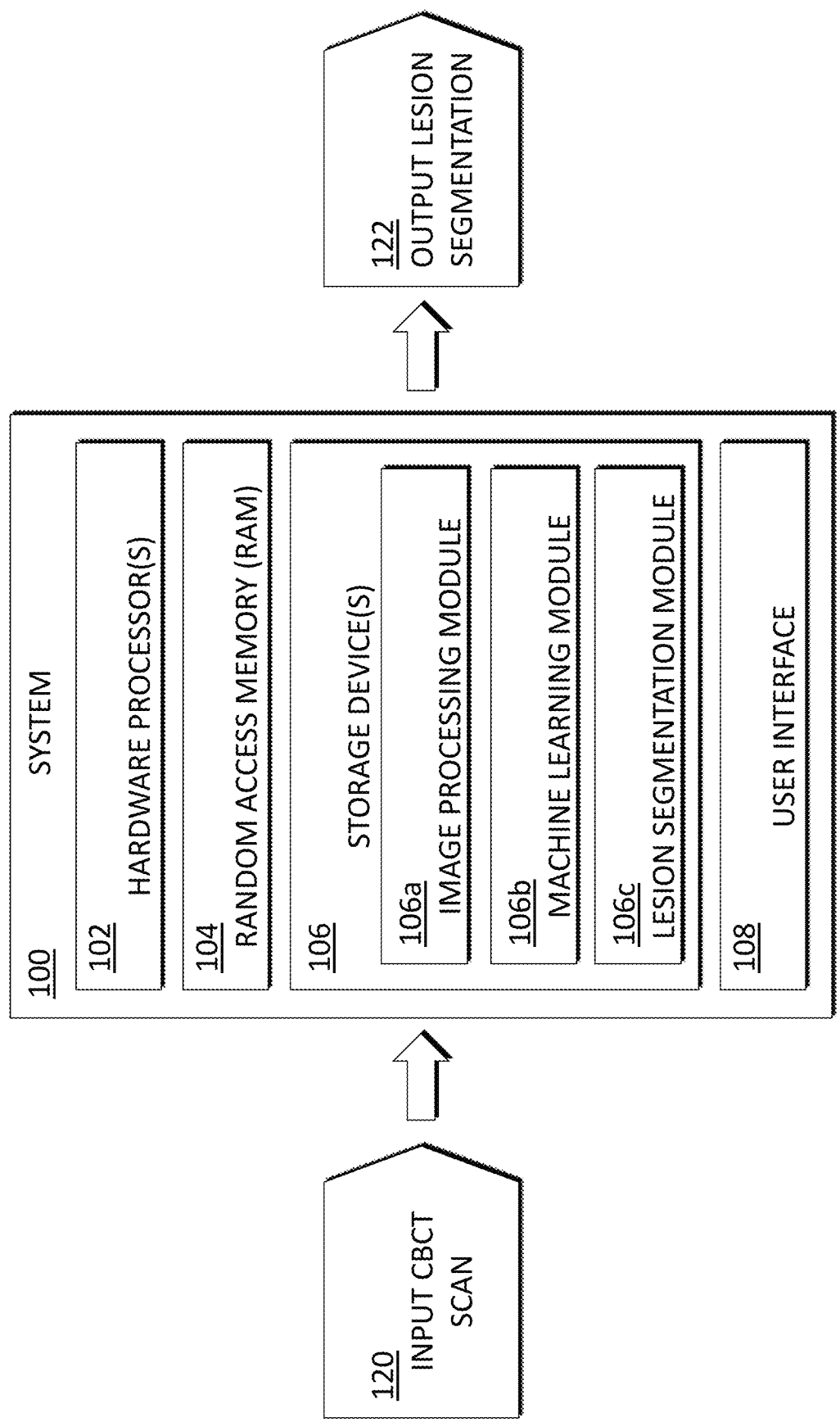
FIG. 1 is a block diagram of an exemplary system for automated detection and segmentation of maxillofacial bone lesions in a subject, based on a volumetric scan obtained by cone beam computerized tomography (CBCT) imaging, in accordance with some embodiments of the present invention.

Disclosed herein is a technique, embodied in a system, method, and computer program product, for automated detection and segmentation of maxillofacial bone lesions in volumetric scans performed by cone beam computerized tomography (CBCT) imaging.

CBCT is a radiographic imaging method that provides three-dimensional (3D) imaging. The CBCT technique consists of the use of a cone shaped X-ray beam producing a single scan, where the X-ray source and a reciprocating array of detector move simultaneously around the patient's head, when used in the maxillofacial region. Single projection images, known as 'basis' images, are acquired at certain degree intervals, which are similar to lateral cephalometric radiographic images, each slightly offset from one another. The series of 'basis' projection images is referred to as the projection data, on which image processing algorithms are applied to generate a 3D volumetric data set. The CBCT 3D volumetric dataset can then provide a successive series of reconstruction images in all three orthogonal planes—coronal, sagittal, and axial.

CBCT technology can provide dental clinicians an imaging modality which is capable of providing a 3D representation of the maxillofacial structures, with minimal distortion and reduced radiation hazards, AS compared to multi-detector CT (MDCT). CBCT is often used as an imaging modality prior to dental implant placement, or to evaluate the location of an impacted tooth. In other cases, CBCT is used to evaluate jaw pathologies, including bone lesions (BLs), such as benign or malignant tumors. However, jaw lesions may also be asymptomatic, and may be found incidentally while viewing a scan performed for another indication.

In some embodiments, the present technique provides for one or more trained machine learning models configured for automated detection and 3D segmentation of BL in CBCT scans.

In a first aspect of the present technique, a machine learning model may be trained to detect and segment BL in one or more individual axial slices of a CBCT scan. In some embodiments, the machine learning model of the present technique may be based on a network architecture comprising a deep learning stage using a Mask-RCNN, followed by gray level filtration and analysis of successive slices.

In some embodiments, the trained machine learning model of the present technique may be trained, validated and tested on a plurality of CBCT scans preformed on a cohort of subjects with and without histologically-confirmed benign BL. In some embodiments, the first exemplary machine learning model of the present technique is trained and tested on a dataset comprising a plurality of axial slices obtained from CBCT scans of a cohort of subjects, representing cases with a variety of histologically confirmed benign BLs that are routinely encountered in practice in maxillofacial CBCT scans, as well as cases without BL. In some embodiments, the CBCT scans used for training the machine learning models of the present technique may be obtained using one or more different CBCT scanners using a variety of scanning protocols.

In a second aspect of the present technique, a machine learning model of the present technique may be trained to detect and segment BL in 3D in volumetric CBCT scans. In some embodiments, the exemplary machine learning model of the present technique may be is based on an architecture comprising a 3D patch-based CNN.

In some embodiments, the trained machine learning model of the present technique may be trained, validated and tested on a plurality of CBCT scans obtained from a cohort comprising subjects with and without histologically-confirmed benign BL. In some embodiments, the second exemplary machine learning model of the present technique is trained and tested on a dataset comprising a plurality of 3D volumetric CBCT scans of a cohort of subjects representing cases with a variety of histologically confirmed benign bone lesions routinely encountered in practice in maxillofacial CBCT scans, as well as cases without BL. In some embodiments, the CBCT scans used for training the machine learning models of the present technique may be obtained using one or more different CBCT scanners using a variety of scanning protocols.

In some embodiments, the trained machine learning models of the present technique are configured for automated detection and segmentation of maxillofacial benign BL in CBCT scans, independent of lesion size, shape, location or histopathology, as well as irrespective of the type and model of the CBCT scanner used. In some embodiments, the trained machine learning models of the present technique may be configured to detect the precise spatial location of bone lesions, without relying on jaw symmetry, and using various fields of view containing either full or different parts of the jaws. Moreover, the trained machine learning models of the present technique are particularly useful in detecting incidental findings, as they are trained and tested on a clinically-realistic dataset, acquired by various CBCT devices and using different protocols.

FIG. 1 is a block diagram of an exemplary system 100 for automated detection and segmentation of maxillofacial bone lesions in a subject, based on volumetric scans obtained by CBCT imaging, in accordance with some embodiments of the present invention.

In some embodiments, system 100 may comprise a hardware processor 102, and a random-access memory (RAM) 104, and/or one or more non-transitory computer-readable storage device 106. In some embodiments, system 100 may store in storage device 106 software instructions or components configured to operate a processing unit (also 'hardware processor,' 'CPU,' 'quantum computer processor,' or simply 'processor'), such as hardware processor 102. In some embodiments, the software components may include an operating system, including various software components and/or drivers for controlling and managing general system tasks (e.g., memory management, storage device control, power management, etc.) and facilitating communication between various hardware and software components.

The software instructions and/or components operating hardware processor 102 may include instructions for receiving and analyzing multiple scan slices captured by any suitable volumetric imaging system. For example, hardware processor 102 may comprise an image processing module 106a, a machine learning module 106b, and a lesion segmentation module 106c.

Image processing module 106a receives as input an entire volumetric scan or one or more axial slices of a volumetric scan 120, and applies one or more image processing algorithms thereto, e.g., to the volumetric scan as a whole and/or to individual axial slices included therein. In some embodiments, image processing module 106a comprises one or more algorithms configured to perform object detection, classification, segmentation, and/or any other similar operation, using any suitable image processing, algorithm, and/or feature extraction process. The input scan 120 may come from various imaging devices having varying settings, configuration and/or scan acquisition parameters. Depending on the embodiment, the image processing module 106a can route scans through various processing functions, or to an output circuit that sends the processed scans for presentation, e.g., on a display, to a recording system, across a network, or to any other logical destination. The image processing module 106a may apply scan processing algorithms alone or in combination. Image processing module 106a may also facilitate logging or recording operations with respect to an input scan 120.

Machine learning module 106b may comprise any one or more neural networks (i.e., which include one or more neural network layers), and can be implemented to embody any appropriate neural network architecture, e.g., U-Net, Mask R-CNN, DeepLab, and the like. In a particular example, machine learning module 106b may include an input layer followed by a sequence of shared convolutional neural network layers. The output of the final shared convolutional neural network layer may be provided to a sequence of one or more additional neural network layers that are configured to generate the object detection data. However, other appropriate neural network processes may also be used. The output of the final shared convolutional neural network layers may be provided to a different sequence of one or more additional neural network layers. In some embodiments, Machine learning module 106b may be used to train, test, validate, and/or inference one or more machine learning model of the present technique.

Lesion segmentation module 106c may comprise one or more algorithms for detecting and segmenting regions of interest (ROIs) which may contain BL in whole volumetric scans and/or individual scan slices.

In some embodiments, system 100 may further comprise a user interface 108 comprising, e.g., a display monitor for displaying images, a control panel for controlling system 100, and a speaker for providing audio feedback.

System 100 as described herein is only an exemplary embodiment of the present invention, and in practice may be implemented in hardware only, software only, or a combination of both hardware and software. System 100 may have more or fewer components and modules than shown, may combine two or more of the components, or may have a different configuration or arrangement of the components. System 100 may include any additional component enabling it to function as an operable computer system, such as a motherboard, data busses, power supply, a network interface card, a display, an input device (e.g., keyboard, pointing device, touch-sensitive display), etc. (not shown). Components of system 100 may be co-located or distributed, or the system may be configured to run as one or more cloud computing 'instances,' 'containers,' 'virtual machines,' or other types of encapsulated software applications, as known in the art.

Figure 2:
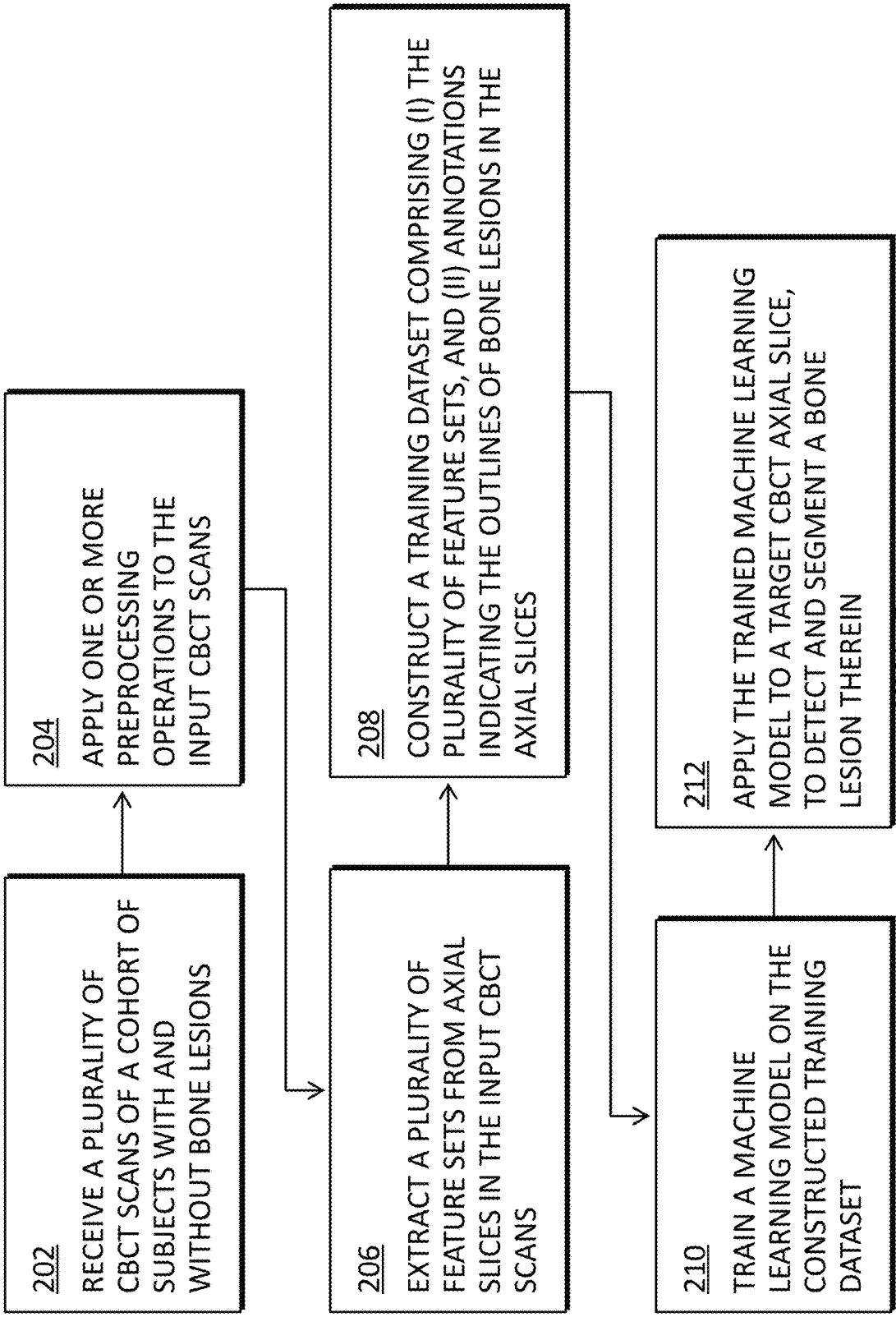
FIG. 2 is a flowchart which illustrates the functional steps in a method for training an exemplary machine learning model configured for automated detection followed by segmentation of maxillofacial bone lesions in axial slices of a volumetric CBCT scans of a subject, in accordance with some embodiments of the present invention.

The instructions of system 100 will now be discussed with reference to the flowchart of FIG. 2 which illustrates the functional steps in a method 200 for training a first exemplary machine learning model of the present technique, configured for automated detection and segmentation of maxillofacial bone lesions in individual axial slices of a volumetric CBCT scan of a subject, according to some embodiments of the present disclosure.

The various steps of method 200 will be described with continuous reference to exemplary system 100 shown in FIG. 1. The various steps of method 200 may either be performed in the order they are presented or in a different order (or even in parallel), as long as the order allows for a necessary input to a certain step to be obtained from an output of an earlier step. In addition, the steps of method 200 may be performed automatically (e.g., by system 100 of FIG. 1), unless specifically stated otherwise. In addition, the steps of method 200 are set forth for exemplary purposes, and it is expected that modification to the flow chart is normally required to accommodate various network configurations and network carrier business policies.

Method 200 begins in step 202, wherein the instructions of image processing module 106a may cause system 100 to receive, as input, a dataset comprising a plurality of CBCT scans associated with a cohort of subjects. In some embodiments, CBCT scan comprises a series of successive axial scan slices. In some embodiments, the input CBCT scans include at least (i) CBCT scans associated with a first subgroup of the cohort of subjects, representing cases demonstrating various jaw lesions of different radiographic appearances, as diagnosed by maxillofacial radiologists and confirmed by histopathological examinations, and (ii) CBCT scans associated with a second subgroup of the cohort of subject, representing cases without bone lesions.

In one exemplary embodiment, the first subgroup of cohort subjects may include cases selected to represent a wide range of subject demographics and lesion parameters and characteristic, including, but not limited to, based on:
  Demographics: The first subgroup may comprise subjects of both sexes and all ages (e.g., between 4-80 years).
  Lesion care prioritization: The first subgroup may comprise cases with varying degrees of urgency, including cases requiring urgent care.
  Lesion category: The first subgroup may comprise cases with lesions categorized as either malignant or benign.
  Lesion radiographic features: The first subgroup may comprise cases exhibiting various radiographic features, including, but not limited to:
    Defined versus non-defined lesion borders,
    hypodense internal lesion structure,
    mixed internal lesion structure, and/or
    hyperdense internal lesion structure.
  Lesion histopathology: The first subgroup may comprise cases having bone lesions associated with one or more pathology types, including, but not limited to:
    Keratocystic Odontogenic Tumor (KOT),
    Radicular Cyst (RC),
    Simple Bone Cyst (SBC),
    Ameloblastic Fibroma (AF),
    Ossifying Fibroma (OF),
    Adenomatoid Odontogenic Cyst (AOC),
    Dentigerous Cyst (DC),
    Cystic Ameloblastoma (Cam),
    Nasopalatine Cyst (NC), and
    Lateral Periodontal Cyst (LPC).
  Lesion site: The first subgroup may comprise cases having bone lesions located at one or more of the following sites:
    The anterior region,
    the premolar region,
    the molar region,
    the ascending ramus, and
    adjacent to the inferior alveolar nerve.
  Lesion follicularity: The first subgroup may comprise cases having follicular bone lesions and non-follicular bone lesions.
  Lesion dimensions: The first subgroup may comprise cases having bone lesions with the following dimensions:
    Maximal lesion diameter between 7-63 mm (mean 23.07±11.99 mm).
    minimal lesion diameter between 3-18 mm (mean 7.85±3.36 mm).

In some embodiments, the received dataset may comprise CBCT scans representing a wide variety of scanning settings and parameters, including with respect to:
  Imaging device: The received dataset may comprise CBCT scans acquired using a variety of CBCT scanner, e.g., iCAT, Morita, Cranex, etc.
  Field of view: The received dataset may comprise CBCT scans acquired using various field of view diameter settings, e.g., between 4-14 cm.
  Number of slices: The number of the axial slices per CBCT scan may range between 100-1,000 slices.
  Voxel size: The received dataset may comprise CBCT scans acquired using various voxel size settings, e.g., between 0.04-0.5 mm.
  Rotation: The received dataset may comprise CBCT scans acquired using various rotation settings, e.g., between 180 degrees (half rotation) and 360 degrees (full rotation).
  Tube voltage and current: The received dataset may comprise CBCT scans acquired using various tube voltage and current settings, e.g., voltage between 85-120 kV, and current between 3-16 mAmp.

In one exemplary instance, as will be described below under "Experimental Results," the present inventors obtained a plurality of CBCT cases associated with a cohort of subjects which includes (i) a first subgroup comprising 41 subjects having each one or more bone lesions exhibiting different characteristics, and (ii) a second subgroup comprising 41 subjects having no bone lesions. The first subgroup includes subjects exhibiting generally well-defined hypodense benign BL, with or without bone expansion, wherein the CBCT scans of this subgroup are performed prior to surgical intervention.

Table 1 below summarizes the details of an exemplary CBCT dataset with respect to demographics, scan parameters and BL characteristics. (Abbreviations: BL=Bone lesion, w/o BL=without bone lesion, IAN=Inferior Alveolar Nerve, RC=Radicular Cyst, KOT=Keratocystic Odontogenic Tumor, DC=Dentigerous Cyst, AF=Ameloblastic Fibroma, OF=Ossifying Fibroma, CAm=Cystic Ameloblastoma, NC=Nasopalatine Cyst, LPC=Lateral Periodontal Cyst, AOT=Adenomatoid Odontogenic Tumor, SBC=Simple Bone Cyst).

TABLE 1

| CATEGORY | PARAMETER | SUBJECTS WITH BL | SUBJECTS WITHOUT BL |
|---|---|---|---|
| Dataset | Number of Scans | 41 | 41 |
|  | Number of slices with BL | 4,555 | 0 |
|  | Number of slices without BL | 10,938 | 16,046 |
| Demographics | Sex (male/female) | 22:19 | 26:15 |
|  | Age (mean and SD) | 33 ± 18.9 | 56 ± 16 |
|  | Age (range) | 3-68 | 19-79 |
| Scan Parameters | Scanner make (i-CAT/Morita/Cranex) | 4:28:9 | 12:28:1 |
|  | Field of view (small/medium/large) | 20:14:7 | 8:17:16 |
|  | Voxel size (mm) | 0.08-0.25 | 0.08-0.25 |
|  | Rotation (180/360 degrees) | 32:9 | 38:3 |
|  | Current (ma) | 6.4 ± 2.4 | 5.6 ± 0.9 |
| Radiographic features of bone lesion | Ant/PM/Molar/Ascend | 12:12:13:4 | — |
|  | Follicular/Non-follicular | 12:29 | — |
|  | Adjacent to IAN (%, No.) | 58.5% (N = 24) | — |
|  | Minimal diameter (Mean ± SD, Range) (mm) | 7.9 ± 3.4 (3-18) | — |
|  | Maximal diameter (Mean ± SD, Range) (mm) | 23.1 ± 12.0 (7-63) | — |
|  | Histopathology of the lesion (number of cases) | RC(14), KOT(13), DC(6), AF(2), OF(1), CAm(1), NC(1), LPC(1), AOT(1), SBC(1) | — |

With reference back to FIG. 2, in step 204, the instructions of image processing module 106*a* may cause system 100 to perform a data preprocessing stage with respect to the CBCT scans in the dataset received in step 202, comprising at least one of data cleaning and normalizing, removal of missing data, data quality control, data augmentations, and/or any other suitable preprocessing method or technique.

For example, data cleaning operations may include removal of entire CBCT scans and/or individual axial slices from a CBCT scan, representing artefacts, such as movement artefacts. In some cases, specific artefacts may be retained, such as those exhibiting the presence of metal artefacts. This is because metal artefacts are very common in CBCT scans, and therefore should preferably be represented in dataset of CBCT axial slices intended for machine learning training purposes.

In some embodiments, other preprocessing operations may include image resizing, converting into one or more desired image formats, adjusting for color or other parameters, and/or modifying in any other suitable manner.

In some embodiments, data augmentation operations may be implemented to increase the number of axial scans within the dataset received in step 202, by adding slightly modified copies of already existing slices. For example, new versions of existing axial slices may be created by translation, rotation, mirroring, or any other suitable manipulation.

In some embodiments, in step 206, the instructions of image processing module 106*a* may cause system 100 to perform a feature extraction and selection stage. In some embodiments, feature extraction includes the generation of a feature set with respect to each of at least some of the axial slices in the dataset received in step 202 and preprocessed in step 204, based on analysis and processing of the input slice images and associated datapoints associated therewith.

In some embodiments, feature extraction stage 206 may be performed using a feature pyramid network (FPN), which is configured to take an input image of a specified scale, and output proportionally-sized feature maps at multiple resolution levels in a fully convolutional fashion. This process builds feature pyramids which may then be used in tasks such as object detection and segmentation in images.

Figure 3:
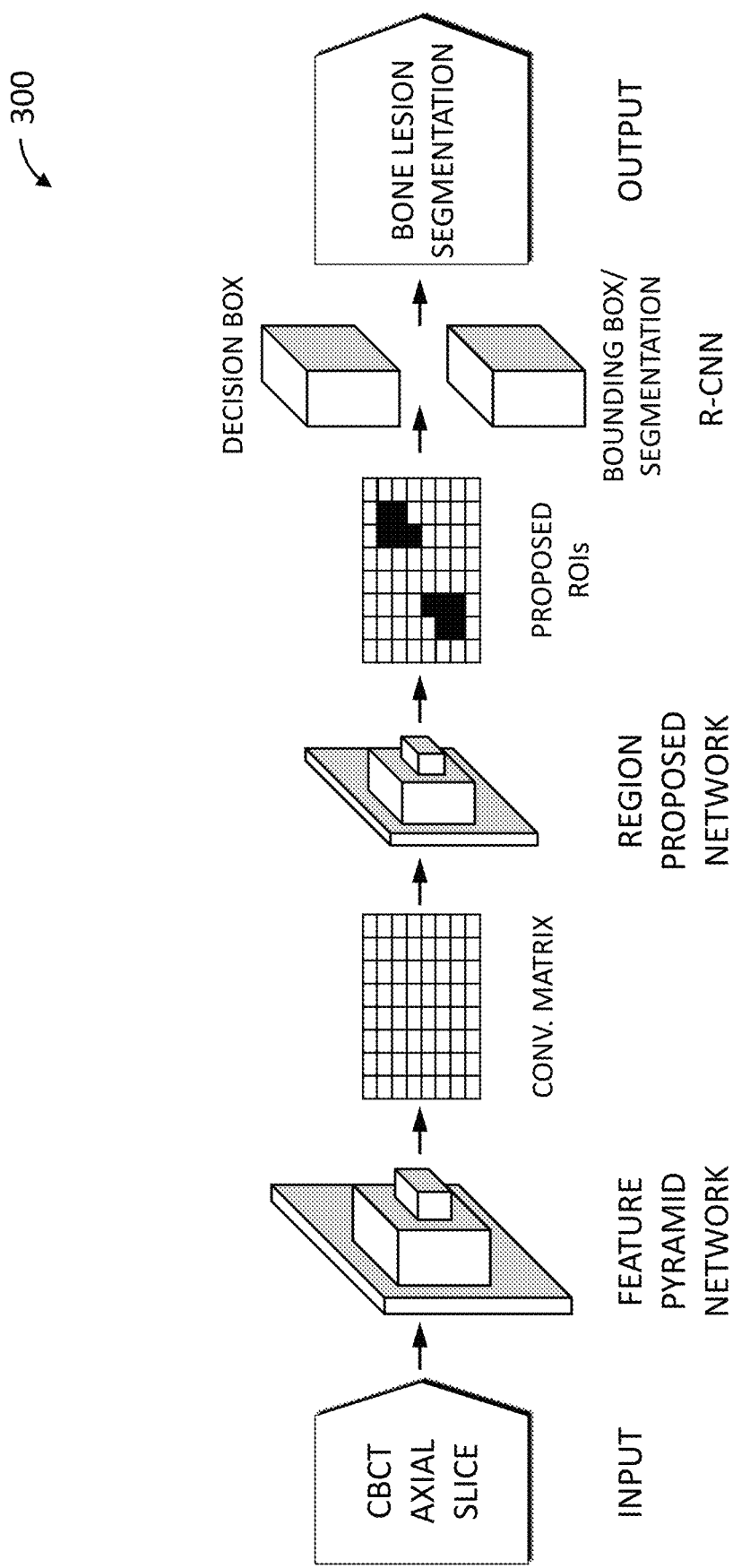
FIG. 3 illustrates an exemplary network architecture which may be utilized by the present technique for training and inferencing a machine learning model configured for automated detection and segmentation of maxillofacial bone lesions in volumetric CBCT scans of a subject, in accordance with some embodiments of the present invention.

Reference is made to FIG. 3, which illustrates an exemplary network architecture 300 which may be utilized by the present technique for training and inferencing a machine learning model configured for automated detection and segmentation of maxillofacial bone lesions in individual axial slices of volumetric CBCT scans of a subject, according to some embodiments of the present disclosure. As can be seen in FIG. 3, exemplary network 300 may comprise a first module comprising a feature pyramid network (FPN) for feature extraction from each input CBCT axial slice. In one example, the present technique may implement a ResNet 101 as an FPN backbone, which may be pre-trained on an image dataset such as the Common Objects in Context (COCO) dataset (see, e.g., Lin T Y, et al. Microsoft COCO: Common objects in context. In: Lecture Notes in Computer Science (including subseries Lecture Notes in Artificial Intelligence and Lecture Notes in Bioinformatics). 2014.30).

With reference back to FIG. 2, in step 208, the instructions of machine learning module 106*b* may cause system 100 to construct one or more training datasets comprising:
 (i) The set of features extracted in step 206 with respect to the input axial slices, and
 (ii) annotations indicating the boundaries/outlines of bone lesions in each of these axial slices.

In some embodiments, the annotations include at least one of: a bounding box enclosing each of the bone lesions, and/or an indication of the exact outline or contour of each of the bone lesions. In some embodiments, the annotations may be made manually, by trained annotators, directly on the input axial slices. In some embodiments, the annotations may be reviewed and validated by experienced specialists, such as oral maxillofacial radiologists.

In some embodiments, the annotations may include additional annotations pertaining to at least one of:
 Lesion care prioritization: The degree of care urgency associated with the lesion.
 Lesion radiographic features: Radiographic features associated with the lesion including, but not limited to:
  defined versus non-defined lesion borders,
  hypodense internal lesion structure,
  mixed internal lesion structure, and/or
  hyperdense internal lesion structure.

Accordingly, in some embodiments, a first exemplary training dataset constructed in step 208 may include (i) image features extracted from the input axial slices, and (ii) indications of the physical boundaries/outlines of bone lesions in each of these axial slices.

In some embodiments, a second exemplary training dataset constructed in step 208 may include (i) image features extracted from the input axial slices, (ii) indications of the physical boundaries/outlines of bone lesions in each of these axial slices, and (iii) lesion care prioritization level (e.g., whether the lesion warrants urgent care). In some embodiments, the lesion care prioritization annotation may be expressed as a binary indication (e.g., urgent/non-urgent), or on a discreet scale indicating prioritization levels from least urgent to most urgent (e.g., a scale of 1-5 or similar).

In some embodiments, a third exemplary training dataset constructed in step 208 may include (i) image features extracted from the input axial slices, (ii) indications of the physical boundaries/outlines of bone lesions in each of these axial slices, and (iii) lesion pathological category (e.g., malignant or benign). In some embodiments, the lesion category may be expressed as a binary indication (e.g., malignant/benign), or on a discreet scale indicating malignancy (e.g., a scale of 1-5 or similar).

In some embodiments, a fourth exemplary training dataset constructed in step 208 may be constructed with respect to only one sub-category of lesions (e.g., well-defined lesions only, or ill-defined lesions only). Such training dataset may include (i) image features extracted from the input axial slices, and (ii) indications of the physical boundaries/outlines of bone lesions in each of these axial slices. In such case, the type of boundaries/outline annotation may be selected to correspond to the lesion sub-category (e.g., exact outline or contour for well-defined lesions, bounding boxes for ill-defined lesions).

In some embodiments, the exemplary training datasets constructed in step 208 may be divided into a training portion, a validation portion, and/or a testing portion.

In some embodiments, in step 210, the instructions of machine learning module 106b may cause system 100 to train a machine learning model of the present technique on one of the constructed in step 208.

In some embodiments, a machine learning model trained on the first exemplary training dataset constructed in step 208 may be configured to detect and segment bone lesions in axial slices obtained from a CBCT scan.

In some embodiments, a machine learning model trained on the second exemplary training dataset constructed in step 208 may be configured to detect and segment bone lesions in axial slices obtained from a CBCT scan, as well as to predict lesion care prioritization level, e.g., as a binary indication (e.g., urgent/non-urgent), or on a discreet scale indicating prioritization levels from least urgent to most urgent (e.g., a scale of 1-5 or similar).

In some embodiments, a machine learning model trained on the third exemplary training dataset constructed in step 208 may be configured to detect and segment bone lesions in axial slices obtained from a CBCT scan, as well as to predict lesion pathological category as malignant or benign, e.g., as a binary indication (e.g., malignant/benign), or on a discreet scale indicating malignancy levels (e.g., a scale of 1-5 or similar).

In some embodiments, a machine learning model trained on the fourth exemplary training dataset constructed in step 208, may be configured to detect and segment bone lesions in axial slices obtained from a CBCT scan based on the sub-category of lesions (e.g., well-defined lesions only, or ill-defined lesions only) included in the training dataset. For example, if the training dataset included well-defined lesions, the output segmentation may be an exact outline or contour of the detected lesion. conversely, if the training dataset included ill-defined lesions, the output segmentation may be a bounding box enclosing the detected bone lesion.

In some embodiments, the machine learning model may comprise any one or more neural networks (i.e., which include one or more neural network layers), and can be implemented to embody any appropriate neural network architecture, e.g., U-Net, Mask R-CNN, DeepLab, and the like.

In some embodiments, a machine learning model of the present technique may be based on an exemplary network architecture, such as exemplary network 300 in FIG. 3, configured to perform object instance detection in an image with simultaneous segmentation for each instance.

With reference back to FIG. 3, exemplary architecture 300 may comprise a series of modules. A second network module (subsequent to the FPN module discussed with reference to step 206 in FIG. 2) may be a deep fully convolutional region proposed network (RPN) that proposes regions of interest (ROIs) in the input images for consideration by a subsequent detection network. A subsequent third module may be a detection and segmentation network based on a Mask R-CNN algorithm, which comprises parallel branches for bounding box recognition and predicting an object mask. In some embodiments, the detection and segmentation network may be realized using lesion segmentation module 106c of system 100. In some embodiments, the RPN outputs a set of ROI proposals over the input axial slice, each with an associated confidence score. This output is used by a region-based object detection R-CNN to detect all objects in the image, while simultaneously precisely segmenting each instance. In some embodiments, the minimum confidence level for categorizing an ROI as containing a bone lesion in a CBCT axial slice may be set to 85%.

In some embodiments, the Mask R-CNN network algorithm may be trained using Stochastic Gradient Descent (SGD) optimization, for minimizing the loss of the model, for example, with a momentum of 0.9, starting with a learning rate of 0.001 and ending with a learning rate of 0.0001. In some embodiments, the training process may comprise, e.g., 60 epochs and 6,000 steps per epoch.

With reference back to FIG. 2, in step 212, the instructions of machine learning module 106b and lesion segmentation module 106c may cause system 100 to perform an inference stage, wherein the trained machine learning model of the present technique may be applied to one or more target axial slices obtained from target volumetric scan 120 (shown in FIG. 1), to output detection and segmentation results 122 of one or more bone lesion represented in the target slice.

In some embodiments, the detection and segmentation results 122 comprise detecting and segmenting regions of interest (ROIs) within one or more axial slices, wherein the ROIs may contain BL.

In some embodiments, inference stage 212 may produce detection and segmentation results which correspond to the training dataset used for training the machine learning model.

For example, a machine learning model trained on the first exemplary training dataset constructed in step 208 may be configured to detect and segment bone lesions in axial slices obtained from a CBCT scan.

In some embodiments, a machine learning model trained on the second exemplary training dataset constructed in step 208 may be configured to detect and segment bone lesions in target axial slices obtained from target volumetric scan 120, as well as to predict lesion care prioritization level, e.g., a binary indication (e.g., urgent/non-urgent), or on a discreet scale indicating care prioritization levels from least urgent to most urgent (e.g., a scale of 1-5 or similar).

In some embodiments, a machine learning model trained on the third exemplary training dataset constructed in step 208, may be configured to detect and segment bone lesions in target axial slices obtained from target volumetric scan 120, as well as to predict lesion pathological category as malignant or benign, e.g., as a binary indication (e.g., malignant/benign), or on a discreet scale indicating malignancy levels (e.g., a scale of 1-5 or similar).

In some embodiments, a machine learning model trained on the fourth exemplary training dataset constructed in step 208, may be configured to detect and segment bone lesions in axial slices obtained from target volumetric scan 120, based on the sub-category of lesions (e.g., well-defined lesions only, or ill-defined lesions only) included in the training dataset. For example, if the training dataset included well-defined lesions, the output segmentation may be an exact outline or contour of the detected lesion. conversely, if the training dataset included ill-defined lesions, the output segmentation may be a bounding box enclosing the detected bone lesion.

Figure 4:
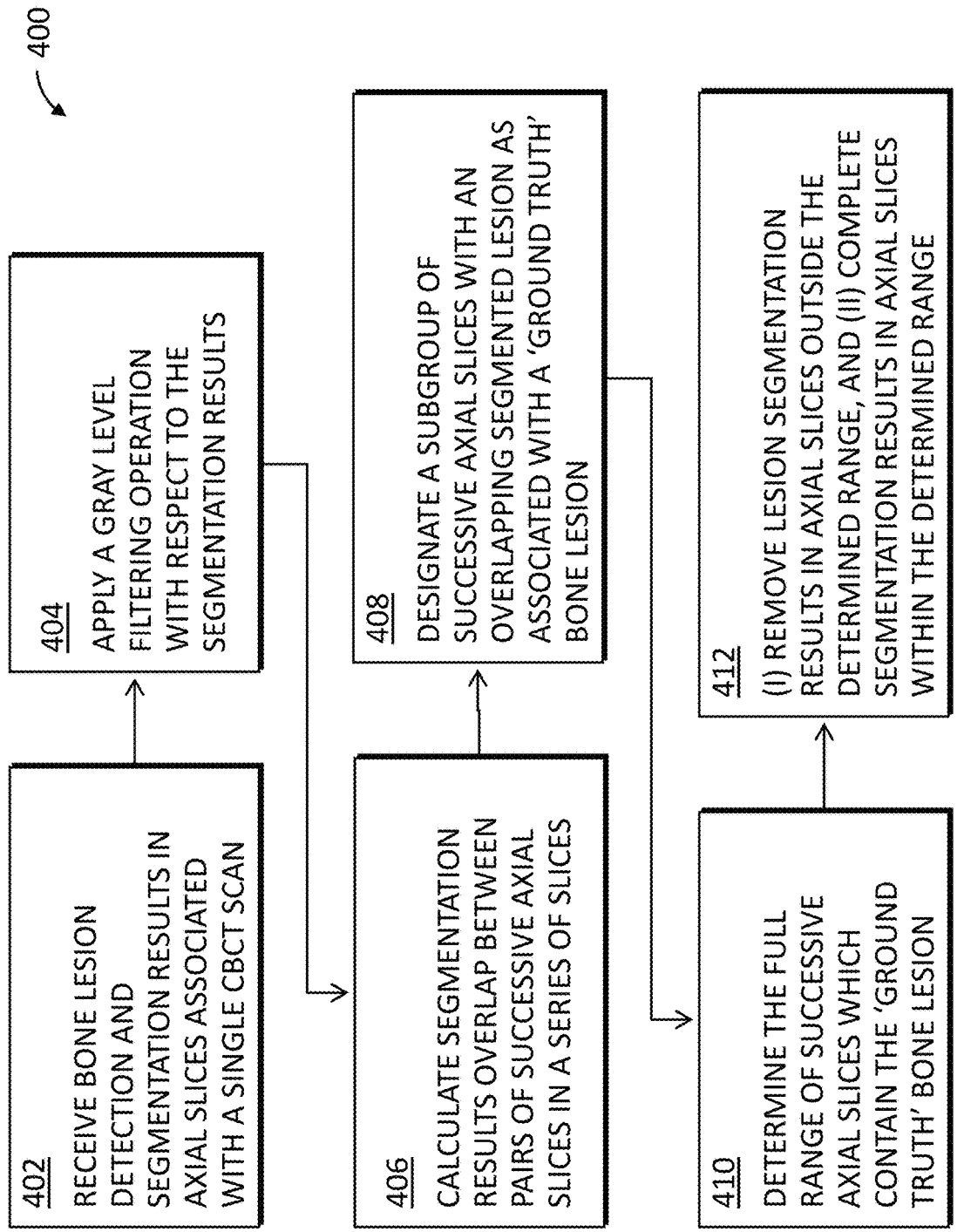
FIG. 4 illustrates the functional steps in a method for performing pair-wise validation of detected bone lesion ROIs across successive slices within a CBCT scan, in accordance with some embodiments of the present invention.

The instructions of system 100 will now be discussed with reference to the flowchart of FIG. 4 which illustrates the functional steps in a method 400 for performing pair-wise validation of detected bone lesion ROIs across successive slices within a volumetric CBCT scan, according to some embodiments of the present disclosure. Method 400 may be used in cases where segmentation results associated with a particular bone lesion in a volumetric CBCT scan may not be consistently indicated across all axial slices in the CBCT case. Method 400 thus provides for eliminating false positive segmentation results in axial slices within a volumetric scan that do not correspond to the physical location of the actual lesion, and to correct, complete or fill-in segmentation results in axial slices with partial or no indication.

The various steps of method 400 will be described with continuous reference to exemplary system 100 shown in FIG. 1. The various steps of method 400 may either be performed in the order they are presented or in a different order (or even in parallel), as long as the order allows for a necessary input to a certain step to be obtained from an output of an earlier step. In addition, the steps of method 400 may be performed automatically (e.g., by system 100 of FIG. 1), unless specifically stated otherwise. In addition, the steps of method 400 are set forth for exemplary purposes, and it is expected that modification to the flow chart is normally required to accommodate various network configurations and network carrier business policies.

Method 400 begins in step 402, wherein system 100 may receive, as input, the inference results 122 of step 212 in method 200 (detailed hereinabove with reference to FIG. 2), wherein the inference results 122 indicate ROI segments representing bone lesions in a successive series of axial slices in an input target volumetric CBCT scan 120. In some embodiments, the ROI indications may comprise an outline or contour segmentation of a detected lesion. In other cases, for example, when machine learning model was trained on a training dataset comprising ill-defined lesions, the ROI indications may be a bounding box enclosing the detected bone lesion.

In step 404, the instructions of image processing module 106a may cause system 100 to perform a filtering operation. In some embodiments, the filtering operation comprises filtering out or removing ROI indications in one or more axial slices within inference results 122, based on the mean gray level value of the indicated ROI. For example, ROIs containing a very bright segmented regions, with a mean gray level value higher than 155, may be removed as potentially representing, e.g., teeth or restorations. Similarly, ROIs containing darker regions, with mean gray level value of less than 50, may also be removed as potentially representing air.

Figure 5B:
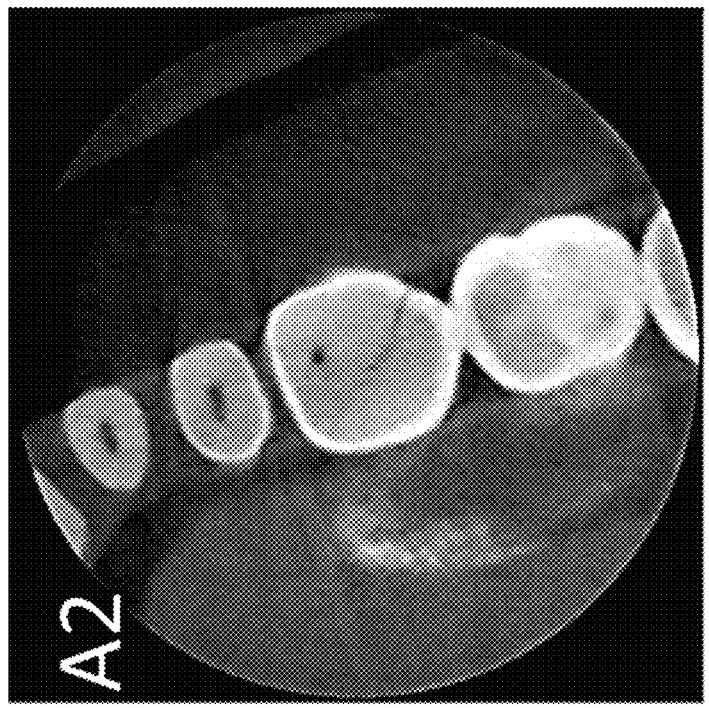
FIGS. 5A-5B show results of a filtering operation of a suspected object with a high attenuation coefficient, in accordance with some embodiments of the present invention.
Figure 5A:
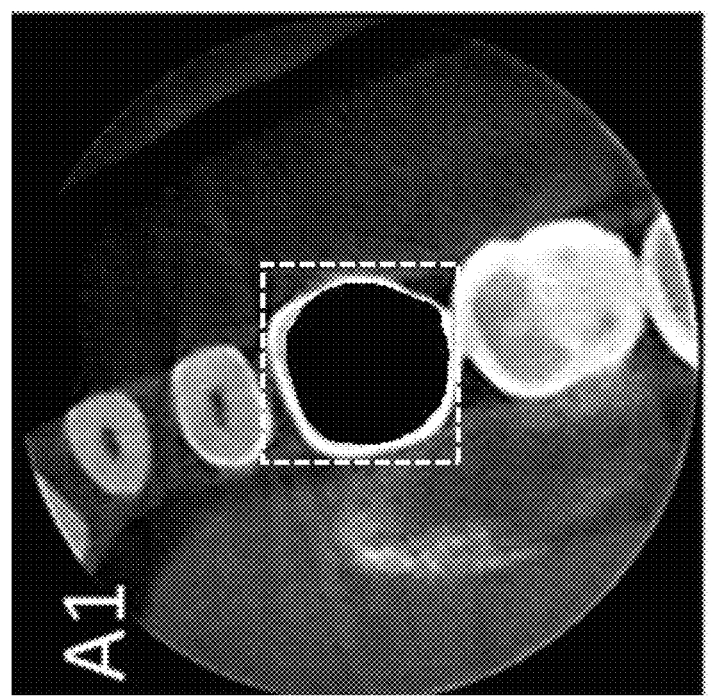
Figure 5D:
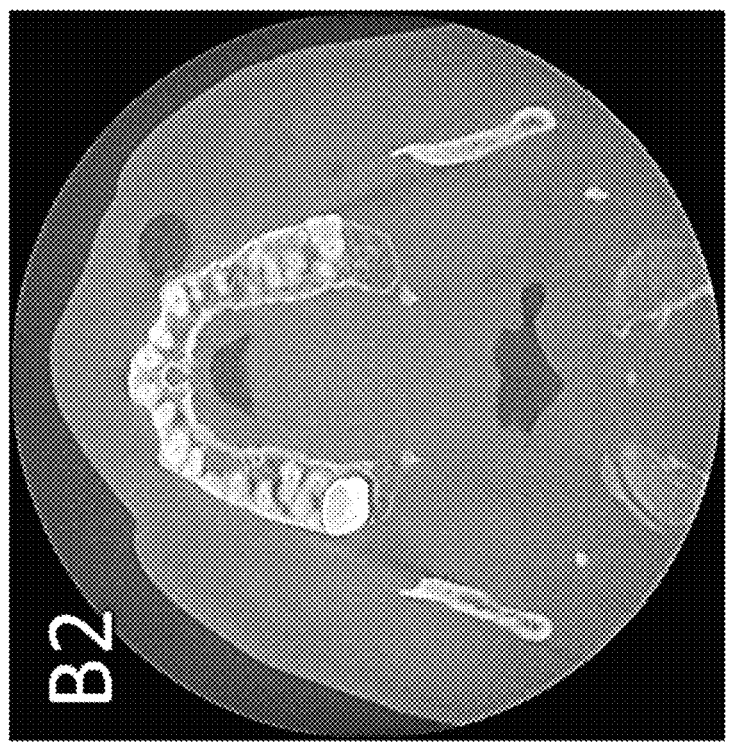
FIGS. 5C-5D show results of the filtering operation of a suspected object with a low attenuation coefficient, in accordance with some embodiments of the present invention.
Figure 5C:
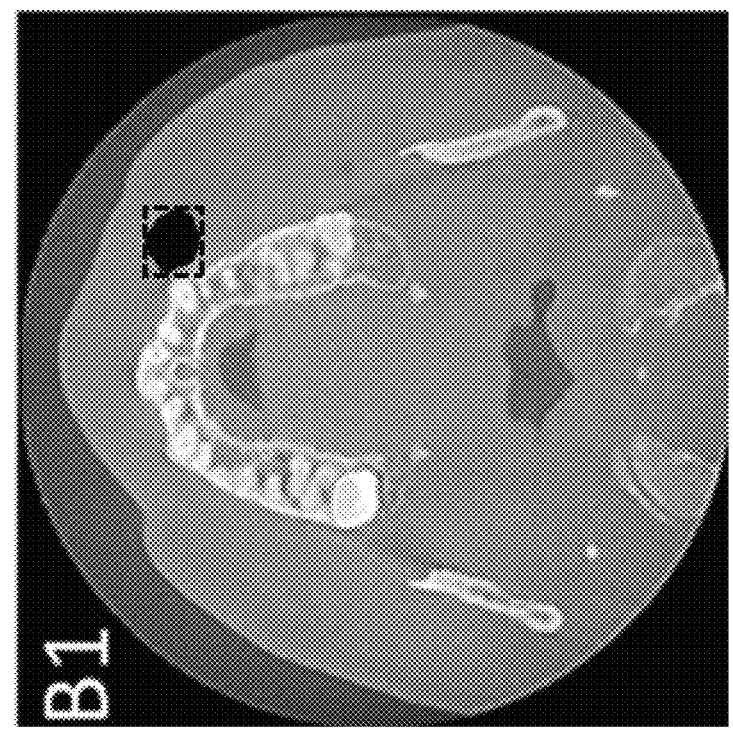

FIGS. 5A-5B show examples of the filtering operation of a suspected object with a high attenuation coefficient. FIG. 5A shows the mask applied at the ROI before the filtering operation, and FIG. 5B after the filtering operation. Similarly, FIGS. 5C-5D shows examples of the filtering operation of a suspected object with a low attenuation coefficient. FIG. 5C shows the mask of the suspected object before and FIG. 5D after the filtering operation.

Method 400 then continues to step 406, wherein system 100 may be configured to calculate a spatial overlap between segmented ROIs in a series of successive pairs of axial slices within the volumetric CBCT scan received in step 402.

In some embodiments, the slice pairs may be consecutive pairs (i.e., a pair of axial slices directly following one another) or non-consecutive pairs (i.e., a pair of axial slices which may be separated by one or more intervening axial slices).

In some embodiments, overlap calculation comprises performing a pair-wise analysis over pairs of slices, which include a current and preceding slice (which may be immediately preceding or separated by one or more intervening slices), to calculate a pixel-wise ROI overlap between each analyzed pair. In some embodiments, an exemplary calculation of pair-wise overlapping ROI pixels may be expressed as:

$$\text{Overlap} = \frac{A \cap B}{A}$$

where A is the number of pixels included in the ROI within the current slice, and A n B is the number of overlapping pixels that are located in identical locations in both the current and preceding slices. FIGS. 6A-6C show an exemplary overlap calculation, according to some embodiments. FIG. 6A shows the detected and segmented ROI pixels in the current slice A, FIG. 6B shows the detected and segmented pixels in the preceding slice B, and FIG. 6C shows the overlap pixels A∩B.

With reference back to FIG. 4, in step 408, system 100 may be configured to designate a subgroup of consecutive axial slices within the series of axial slices, wherein all such consecutive axial slices within the subgroup comprise a detected and segmented ROI having a calculated pair-wise overlap which exceeds a specified threshold (e.g., 50%, or between 30-80%).

In some embodiments, when such subgroup includes at least a specified minimum number of axial slices (e.g., at least 14 axial slices within any series of 20 axial slices), such subgroup may be designated as representing an actual 'ground truth' bone lesion.

In some embodiments, in step 410, system 100 may be configured to determine the full range of consecutive axial slices which contain ROIs associated with the 'ground-truth' bone lesion within the input CBCT case received in step 402. Accordingly, in some embodiments, system 100 may identify the initial and final slices within the CBCT case subgroup which correspond to the 'ground-truth' bone lesion. In some embodiments, the initial axial slice may be defined as the first of at least 6 slices out of 20 successive slices, included in the same subgroup of ROIs. The final slice may be defined as the last slice in the subgroup that fulfilled the same condition (6 out of 20 successive slices).

Figure 7:
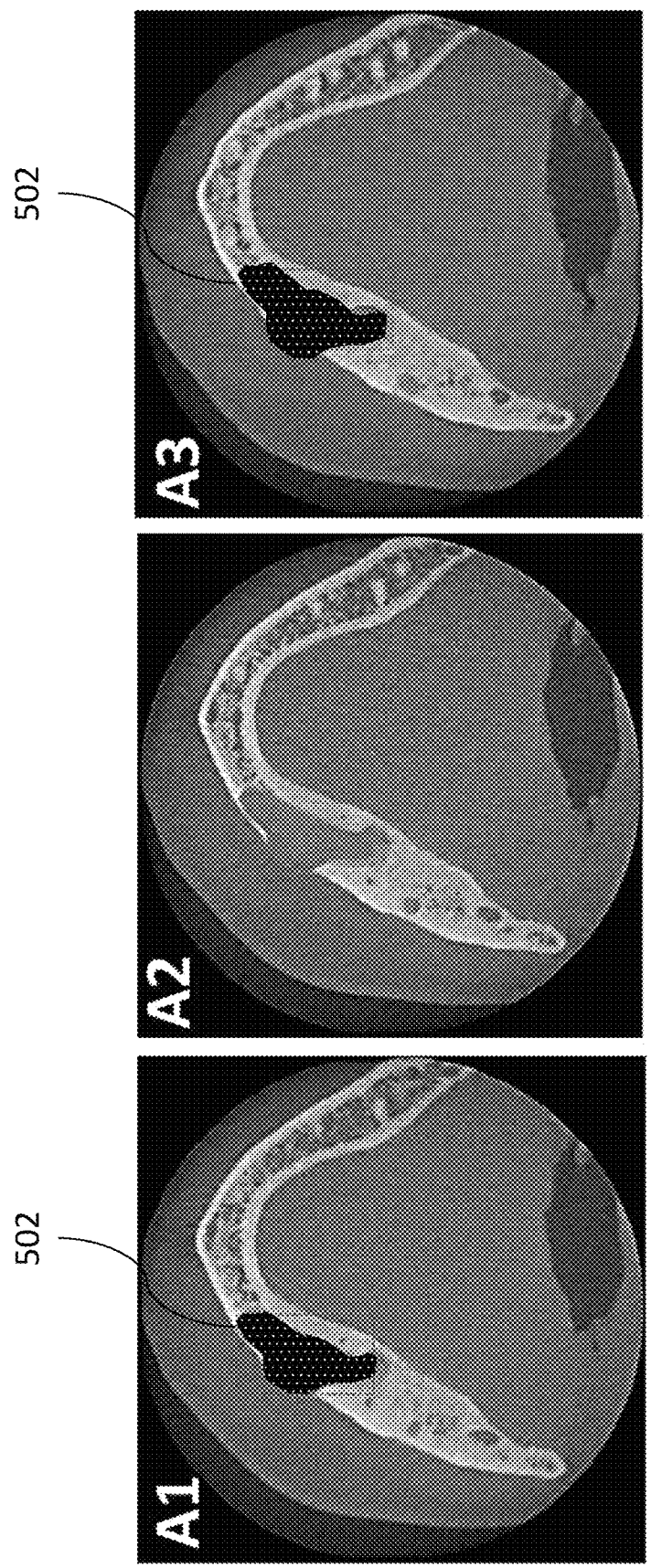

In some embodiments, in step 412, system 100 may be configured to:
Correct or fill-in and complete a bone lesion segment or mask in all the slices included within the subgroup between the initial and final slices designated in step 410, in which the ROI was not originally detected. In some embodiments, this may be performed by interpolating the shape of the detected ROI in the two nearest neighboring slices, based on the assumption that since the mask of the bone lesion should be very similar in consecutive slices. FIG. 7 illustrates this process. Panel A1 shows an axial slice in which a bone lesion mask 502 is detected. Panel A2 is a consecutive axial slice in which the mask is not detected, and panel A3 is a next consecutive slice to the one shown in panel A2, in which mask 502 is detected again. Therefore, system 100 may interpolate the shape of the mask in slice A2 based on the detected ROIs in the two nearest neighboring slices (panels A1 and A3), and insert the interpolated mask in slice A2.

Remove all other detected and segmented ROIs not included in the range of the initial and final slices.

In some embodiments following the detection and segmentation of bone lesions in axial slices obtained from target volumetric scan 120, and the pair-wise validation according to method 400 hereinabove, the instructions of lesion segmentation module 106c may cause system 100 to generate a 3D segmentation of the bone lesion, as shown, for example, in FIG. 11. The volume of the 3D bone lesion may be defined as the product of the voxel volume and the number of the segmented voxels in all of the axial slices.

Figure 8:
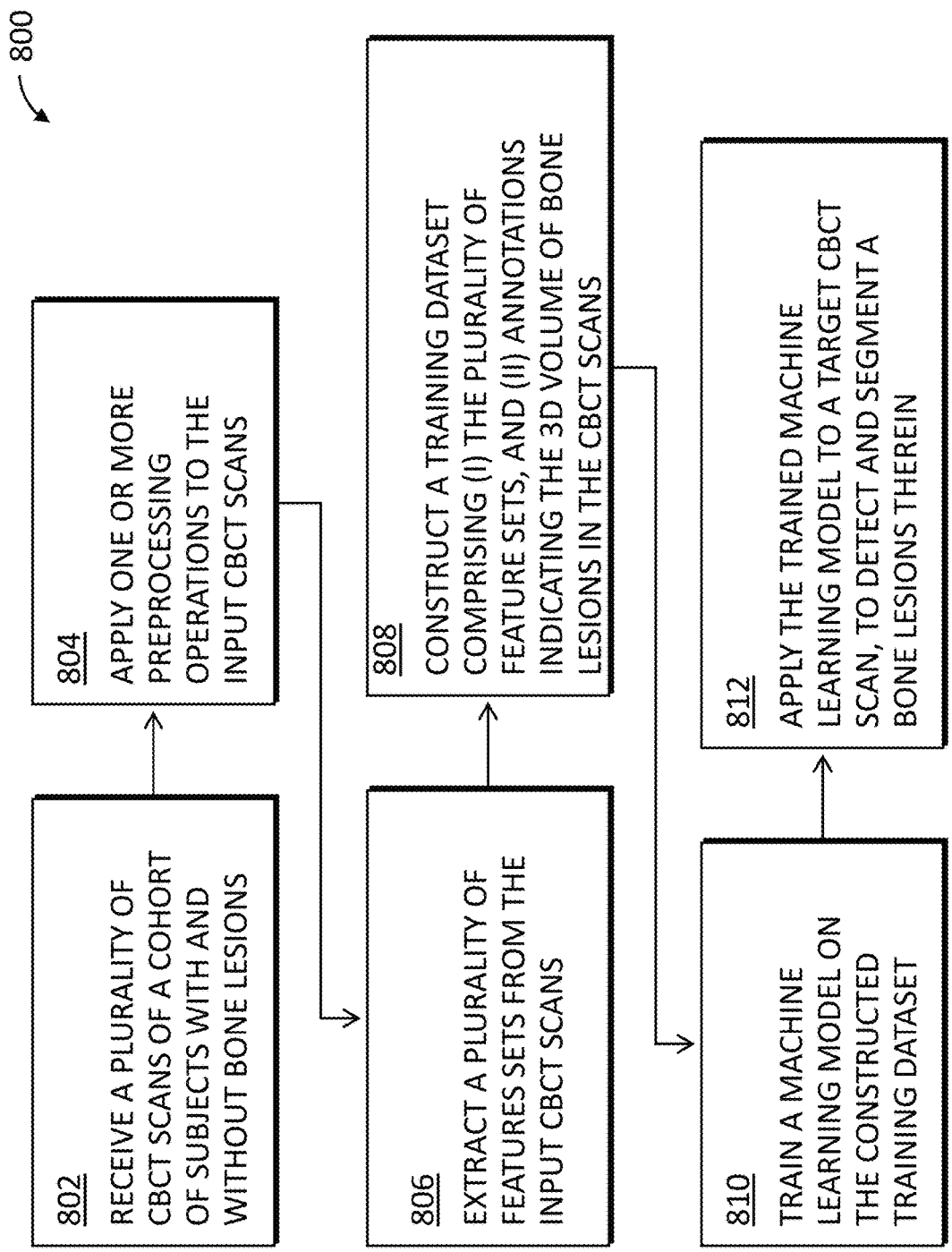
FIG. 8 illustrates the functional steps in a method for training a second exemplary machine learning model of the present technique, configured for automated detection and segmentation of maxillofacial bone lesions in 3D volumetric CBCT scan of a subject, in accordance with some embodiments of the present invention.

The instructions of system 100 will now be discussed with reference to the flowchart of FIG. 8, which illustrates the functional steps in a method 800 for training a machine learning model of the present technique, configured for automated detection and segmentation of maxillofacial bone lesions in 3D volumetric CBCT scan of a subject, according to some embodiments of the present disclosure.

The various steps of method 800 will be described with continuous reference to exemplary system 100 shown in FIG. 1. The various steps of method 800 may either be performed in the order they are presented or in a different order (or even in parallel), as long as the order allows for a necessary input to a certain step to be obtained from an output of an earlier step. In addition, the steps of method 800 may be performed automatically (e.g., by system 100 of FIG. 1), unless specifically stated otherwise. In addition, the steps of method 800 are set forth for exemplary purposes, and it is expected that modification to the flow chart is normally required to accommodate various network configurations and network carrier business policies.

Method 800 begins in step 802, wherein system 100 may receive, as input, a dataset comprising a plurality of volumetric CBCT scans associated with a cohort of subjects. In some embodiments, the volumetric CBCT scans comprise a series of successive axial scan slices. In some embodiments, the input CBCT scans include at least (i) CBCT scans associated with a first subgroup of the cohort of subjects, representing cases demonstrating various jaw lesions of different radiographic appearances, as diagnosed by maxillofacial radiologists and confirmed by histopathological examinations, and (ii) CBCT scans associated with a second subgroup of the cohort of subject, representing cases without bone lesions.

In one exemplary embodiment, the first subgroup of cohort subjects may include CBCT cases selected to represent a wide range of subject demographics, lesion care prioritization levels, lesions categories, lesions radiographic features, lesion histopathology, lesion sites, lesion follicularity, lesion dimensions, and/or other lesion parameters and characteristic, as detailed hereinabove with reference to step 202 in method 200. In some embodiments, the received dataset may comprise CBCT scans representing a wide variety of scanning settings and parameters, including with respect to imaging device used to acquire the scan, the selected field of view, number of slices in the scan, voxel sizes, tube voltage and current, and/or any other scanning settings and parameters, as detailed hereinabove with reference to step 202 in method 200.

With reference back to FIG. 2, in step 804, the instructions of image processing module 106a may cause system 100 to perform a data preprocessing stage with respect to the CBCT scans in the dataset received in step 802, comprising at least one of data cleaning and normalizing, removal of missing data, data quality control, data augmentations, and/or any other suitable preprocessing method or technique.

For example, data cleaning operations may include removal of entire CBCT scans and/or individual axial slices from a CBCT scan, representing artefacts, such as movement artefacts.

In some embodiments, other preprocessing operations may include images resizing, converting into one or more desired image formats, adjusting for color or other parameters, and/or modifying in any other suitable manner.

In some embodiments, data augmentation operations may be implemented to increase the number of CBCT scans within the dataset received in step 802, by adding slightly modified copies of already existing scans.

In some embodiments, in step 806, the instructions of image processing module 106a may cause system 100 to perform a feature extraction and selection stage. In some embodiments, feature extraction includes the generation of a feature set with respect to at least some of the CBCT scans received in step 802 and preprocessed in step 804, based on analysis and processing of their associated slice images and any other datapoints associated therewith.

Figure 9:
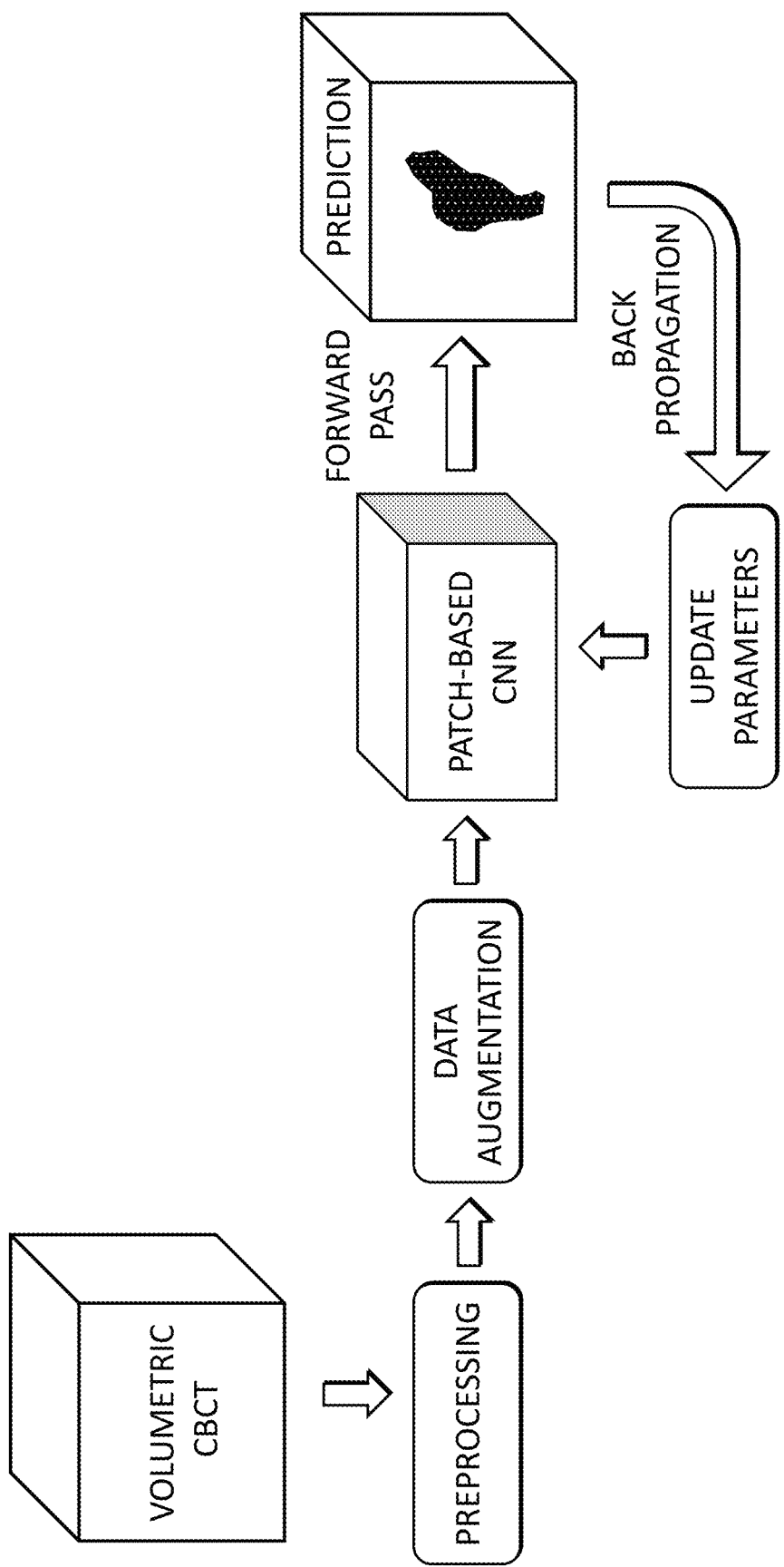
FIG. 9 illustrates another exemplary network architecture which may be utilized by the present technique for training and inferencing a machine learning model configured for automated detection and segmentation of maxillofacial bone lesions in volumetric CBCT scans of a subject, in accordance with some embodiments of the present invention.

Reference is made to FIG. 9, which illustrates an exemplary network architecture 900 which may be utilized by the present technique for training and inferencing a machine learning model configured for automated detection and segmentation of maxillofacial bone lesions in volumetric CBCT scans of a subject, according to some embodiments of the present disclosure. As can be seen in FIG. 9, exemplary network 900 may comprise a patch-based CNN.

With reference back to FIG. 8, in step 808, the present technique provides for constructing a training dataset comprising:
(i) The sets of features extracted in step 806 with respect to the input volumetric CBCT scans, and
(ii) annotations indicating the volumetric outline of bone lesions in the input volumetric CBCT scans.

In some embodiments, the annotations include at least one of: a bounding box enclosing each of the bone lesions, and/or an indication of the exact volumetric outline or contour of each of the bone lesions.

In some embodiments, the annotations may be made manually, by trained annotators, by annotating the boundaries/outlines of bone lesions directly on individual axial slices comprising each CBCT scans, or using any other suitable method. In some embodiments, the annotations may be reviewed and validated by experienced specialists, such as oral maxillofacial radiologists.

In some embodiments, the annotations may include additional annotations pertaining to at least one of:
Lesion care prioritization: The degree of care urgency associated with the lesion.
Lesion radiographic features: Radiographic features associated with the lesion including, but not limited to:
defined versus non-defined lesion borders,
hypodense internal lesion structure,
mixed internal lesion structure, and/or
hyperdense internal lesion structure.

Accordingly, in some embodiments, a first exemplary training dataset constructed in step 808 may include (i)

image features extracted from the input volumetric CBCT scans, and (ii) indications of the physical boundaries/outlines of bone lesions in each of these volumetric CBCT scans.

In some embodiments, a second exemplary training dataset constructed in step 808 may include (i) image features extracted from the input volumetric CBCT scans, (ii) indications of the physical boundaries/outlines of bone lesions in each of these volumetric CBCT scans, and (iii) lesion care prioritization level (e.g., whether the lesion warrants urgent care). In some embodiments, the lesion care prioritization annotation may be expressed as a binary indication (e.g., urgent/non-urgent), or on a discreet scale indicating prioritization levels from least urgent to most urgent (e.g., a scale of 1-5 or similar).

In some embodiments, a third exemplary training dataset constructed in step 808 may include (i) image features extracted from the input volumetric CBCT scans, (ii) indications of the physical boundaries/outlines of bone lesions in each of these volumetric CBCT scans, and (iii) lesion pathological category (e.g., malignant or benign). In some embodiments, the lesion category may be expressed as a binary indication (e.g., malignant/benign), or on a discreet scale indicating malignancy (e.g., a scale of 1-5 or similar).

In some embodiments, a fourth exemplary training dataset constructed in step 808 may be constructed with respect to only one sub-category of lesions (e.g., well-defined lesions only, or ill-defined lesions only). Such training dataset may include (i) image features extracted from the input volumetric CBCT scans, and (ii) indications of the physical boundaries/outlines of bone lesions in each of these volumetric CBCT scans. In such case, the type of boundaries/outline annotation may be selected to correspond to the lesion sub-category (e.g., exact outline or contour for well-defined lesions, bounding boxes for ill-defined lesions).

In some embodiments, the training dataset constructed in step 808 may be divided into a training portion, a validation portion, and/or a testing portion.

In some embodiments, in step 810, a machine learning model of the present technique may be trained on the training dataset constructed in step 808.

In some embodiments, a machine learning model trained on the first exemplary training dataset constructed in step 808 may be configured to detect and segment bone lesions in volumetric CBCT scans.

In some embodiments, a machine learning model trained on the second exemplary training dataset constructed in step 808 may be configured to detect and segment bone lesions in volumetric CBCT scans, as well as to predict lesion care prioritization level, e.g., as a binary indication (e.g., urgent/non-urgent), or on a discreet scale indicating prioritization levels from least urgent to most urgent (e.g., a scale of 1-5 or similar).

In some embodiments, a machine learning model trained on the third exemplary training dataset constructed in step 808 may be configured to detect and segment bone lesions in volumetric CBCT scans, as well as to predict lesion pathological category as malignant or benign, e.g., as a binary indication (e.g., malignant/benign), or on a discreet scale indicating malignancy levels (e.g., a scale of 1-5 or similar).

In some embodiments, a machine learning model trained on the fourth exemplary training dataset constructed in step 808, may be configured to detect and segment bone lesions in volumetric CBCT scans, based on the sub-category of lesions (e.g., well-defined lesions only, or ill-defined lesions only) included in the training dataset. For example, if the training dataset included well-defined lesions, the output segmentation may be an exact outline or contour of the detected lesion. conversely, if the training dataset included ill-defined lesions, the output segmentation may be a bounding box enclosing the detected bone lesion.

In some embodiments, a machine learning model of the present technique may be based on an exemplary network architecture, such as exemplary network 900 in FIG. 9, configured to perform object instance detection in an image with simultaneous segmentation for each instance.

With reference back to FIG. 8, in step 812, an inference stage may be performed in which the trained machine learning model of the present technique may be applied to a target volumetric CBCT scan 120, to output detection and segmentation results 122 of one or more bone lesion represented in the volumetric CBCT scan.

In some embodiments, inference stage 812 may produce detection and segmentation results 122 which correspond to the training dataset used to training the machine learning model.

For example, a machine learning model trained on the first exemplary training dataset constructed in step 808 may be configured to detect and segment bone lesions in target volumetric CBCT scan 120.

In some embodiments, a machine learning model trained on the second exemplary training dataset constructed in step 808 may be configured to detect and segment bone lesions in target volumetric CBCT scan 120, as well as to predict lesion care prioritization level, e.g., a binary indication (e.g., urgent/non-urgent), or on a discreet scale indicating care prioritization levels from least urgent to most urgent (e.g., a scale of 1-5 or similar).

In some embodiments, a machine learning model trained on the third exemplary training dataset constructed in step 808, may be configured to detect and segment bone lesions in target volumetric CBCT scan 120, as well as to predict lesion pathological category as malignant or benign, e.g., as a binary indication (e.g., malignant/benign), or on a discreet scale indicating malignancy levels (e.g., a scale of 1-5 or similar).

In some embodiments, a machine learning model trained on the fourth exemplary training dataset constructed in step 808, may be configured to detect and segment bone lesions in target volumetric CBCT scan 120, based on the sub-category of lesions (e.g., well-defined lesions only, or ill-defined lesions only) included in the training dataset. For example, if the training dataset included well-defined lesions, the output segmentation may be an exact outline or contour of the detected lesion. conversely, if the training dataset included ill-defined lesions, the output segmentation may be a bounding box enclosing the detected bone lesion.

Experimental Results

The present inventors tested the machine learning model of the present technique, trained according to method 200 detailed hereinabove, on a test portion comprising 22 CBCT scan included in the dataset constructed in step 206 in FIG. 2. The test portion of the dataset comprised 11 control cases and 11 cases with various types of benign BL. The test cases represented a variety of demographics, lesion parameters and characteristic, and scanning settings and parameters, as detailed above with reference to step 202 in FIG. 2.

Figure 10:
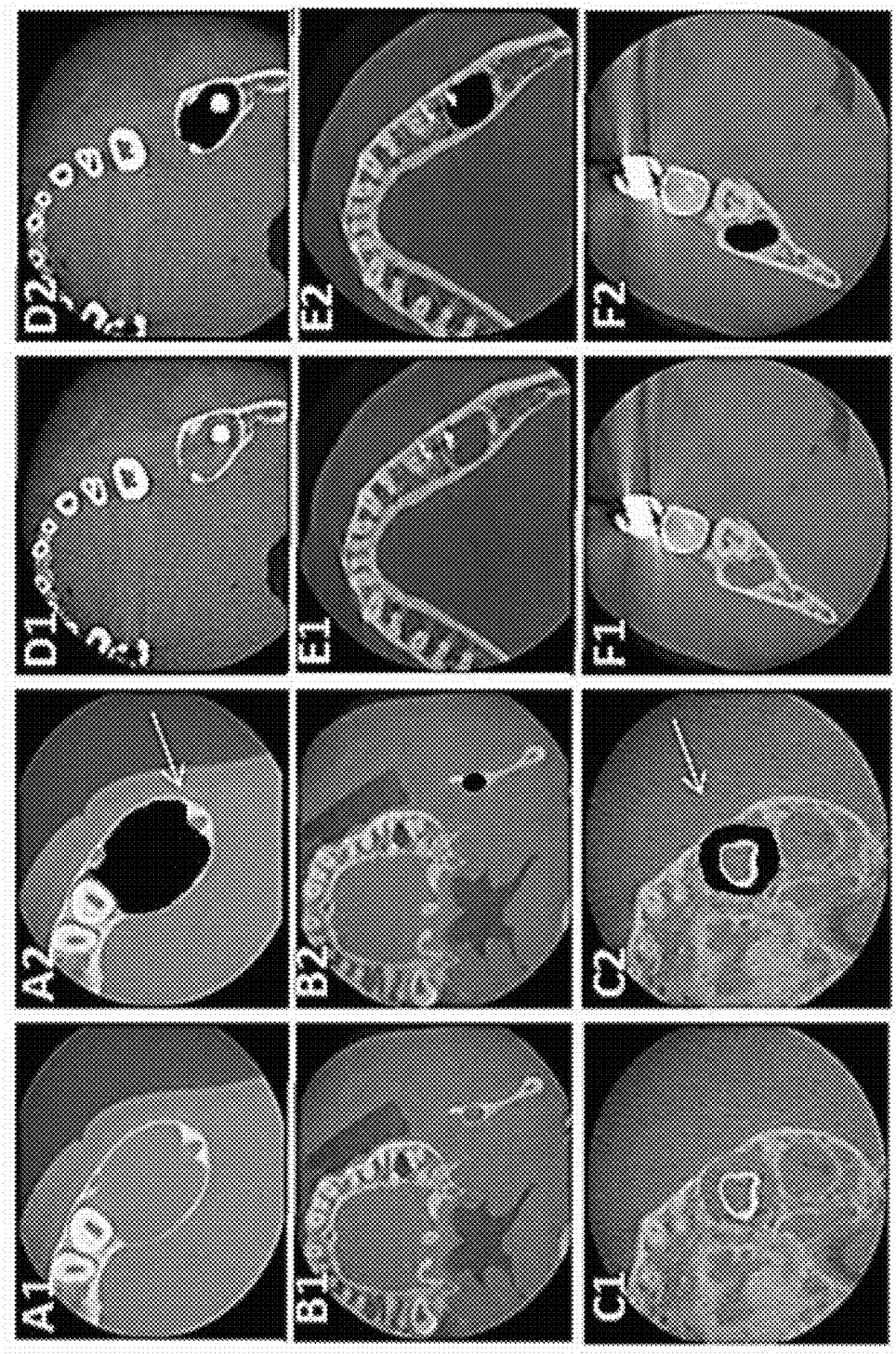
FIGS. 10-11 show experimental results, in accordance with some embodiments of the present invention.

The detection and segmentation results are shown in the examples in FIG. 10, and are summarized in Tables 2A-2B below.

Table 2A shows results of the machine learning model when inferenced on individual axial slices, before the pairwise analysis of sequential slices discussed hereinabove. As shown in Table 2A below, the sensitivity of the trained model ranged between 52.8%-100% per scan, with a total sensitivity of 83.5%. The precision of the model for these cases ranged between 80.8%-100% with a total precision of 88.4%. For the 11 control cases in the test dataset, which included 3445 axial slices altogether, the machine learning model falsely marked 112 objects, with an average of 10.2 false marks in all the slices of one case.

TABLE 2A

| No. | No. of ROIs | Detected ROIs | Missed ROIs | False Positives | Sensitivity | Precision |
|---|---|---|---|---|---|---|
| 1 | 60 | 33 | 27 | 5 | 55.0% | 86.8% |
| 2 | 152 | 131 | 21 | 30 | 86.2% | 81.4% |
| 3 | 80 | 69 | 11 | 16 | 86.3% | 81.2% |
| 4 | 189 | 185 | 4 | 39 | 97.9% | 82.6% |
| 5 | 207 | 198 | 9 | 4 | 95.7% | 98.0% |
| 6 | 194 | 154 | 40 | 31 | 79.4% | 83.2% |
| 7 | 147 | 147 | 0 | 2 | 100.0% | 98.7% |
| 8 | 87 | 81 | 6 | 8 | 93.1% | 91.0% |
| 9 | 86 | 58 | 28 | 9 | 67.4% | 86.6% |
| 10 | 61 | 42 | 19 | 10 | 68.9% | 80.8% |
| 11 | 142 | 75 | 67 | 0 | 52.8% | 100.0% |
| Total | 1405 | 1173 | 232 | 154 | 83.5% | 88.4% |

After the initial detection of suspected objects in each slice, all the slices of a specific CBCT scan were collectively analyzed, in order to evaluate if there is any subgroup of suspected objects that appears in sequential slices and represent a true bone lesion. The results of the subsequent analysis showed that the all the 22 cases in the test dataset were classified correctly with an accuracy of 100%. Specifically, all 11 control cases were classified by the algorithm as cases without BL while the 11 CBCT scans with BL, were classified as containing BL.

Table 2B shows results of the machine learning model when inferenced on individual axial slices, with pair-wise analysis of sequential slices, using the steps of method 400 as detailed hereinabove. For all the CBCT cases which were classified as cases with BL, the initial and final slices including the lesion were automatically identified, and the spatial location of the bone lesion in all the slices was calculated. Then, all the suspected objects that were segmented by the machine learning model but did not overlap the spatial location of the bone lesion were removed. Finally, the model segmented the BL in the slices in which they were missed, by interpolating the masks detected in the nearest neighboring slices. As a result, following the subsequent analysis of the slices in each case, the improved sensitivity ranged between 82.0%-100% with a total sensitivity of 95.9%. The improved precision ranged between 92.4%-100% with a total precision of 98.8%. The results are shown in Table 2B below:

TABLE 2B

| No. | No. of ROIs | Detected ROIS | Missed ROIs | False Positives | Sensitivity | Precision |
|---|---|---|---|---|---|---|
| 1 | 60 | 56 | 4 | 0 | 93.3% | 100.0% |
| 2 | 152 | 152 | 0 | 1 | 100.0% | 99.3% |
| 3 | 80 | 73 | 8 | 0 | 91.3% | 100.0% |
| 4 | 189 | 189 | 0 | 0 | 100.0% | 100.0% |
| 5 | 207 | 207 | 0 | 0 | 100.0% | 100.0% |
| 6 | 194 | 194 | 0 | 16 | 100.0% | 92.4% |
| 7 | 147 | 147 | 0 | 0 | 100.0% | 100.0% |
| 8 | 87 | 82 | 5 | 0 | 94.3% | 100.0% |
| 9 | 86 | 74 | 12 | 0 | 86.0% | 100.0% |
| 10 | 61 | 50 | 11 | 0 | 82.0% | 100.0% |
| 11 | 142 | 123 | 19 | 0 | 86.6% | 100.0% |
| Total | 1405 | 1347 | 59 | 17 | 95.9% | 98.8% |

Figure 11:
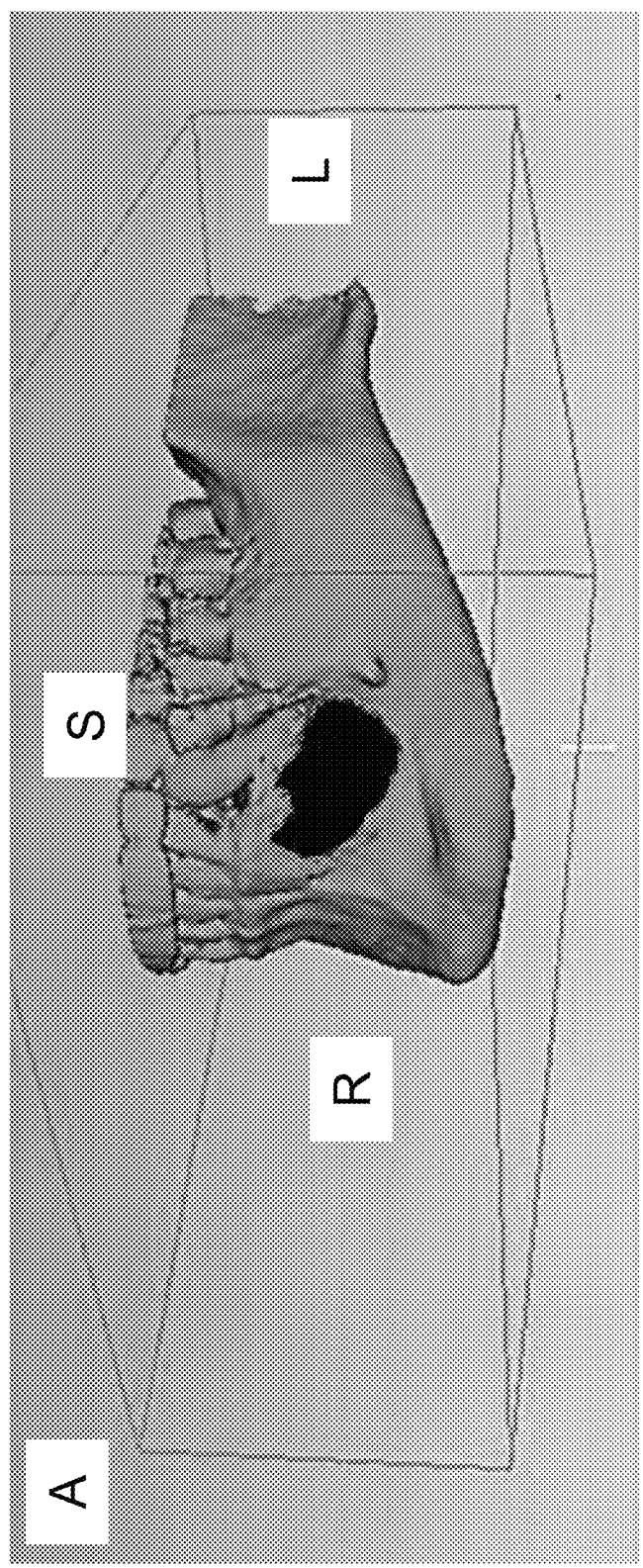

Following the final segmentation of the BL in the relevant CBCT slices, the model generated a 3D segmentation of each bone lesion, as shown in FIG. 11. The volume of the bone lesion, which is important for follow-up, is defined as the product of the voxel volume by the number of the segmented voxels in all the slices. The total time for detecting and segmenting the BL in each CBCT case was between 12-15 minutes, depending on the total number of axial slices analyzed.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, a field-programmable gate array (FPGA), or a programmable logic array (PLA) may execute the computer readable program instructions by utilizing state information of the computer readable program instructions to personalize the electronic circuitry, in order to perform aspects of the present invention. In some embodiments, electronic circuitry including, for example, an application-specific integrated circuit (ASIC), may be incorporate the computer readable program instructions already at time of fabrication, such that the ASIC is configured to execute these instructions without programming.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In the description and claims, each of the terms "substantially," "essentially," and forms thereof, when describing a numerical value, means up to a 20% deviation (namely, ±20%) from that value. Similarly, when such a term describes a numerical range, it means up to a 20% broader range—10% over that explicit range and 10% below it).

In the description, any given numerical range should be considered to have specifically disclosed all the possible subranges as well as individual numerical values within that range, such that each such subrange and individual numerical value constitutes an embodiment of the invention. This applies regardless of the breadth of the range. For example, description of a range of integers from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 4, and 6. Similarly, description of a range of fractions, for example from 0.6 to 1.1, should be considered to have specifically disclosed subranges such as from 0.6 to 0.9, from 0.7 to 1.1, from 0.9 to 1, from 0.8 to 0.9, from 0.6 to 1.1, from 1 to 1.1 etc., as well as individual numbers within that range, for example 0.7, 1, and 1.1.

The descriptions of the various embodiments of the present invention have been presented for purposes of illustration, but are not intended to be exhaustive or limited to the explicit descriptions. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise," "include," and "have," as well as forms thereof, are not necessarily limited to members in a list with which the words may be associated.

Where there are inconsistencies between the description and any document incorporated by reference or otherwise relied upon, it is intended that the present description controls.

What is claimed is:

1. A system comprising:
   at least one hardware processor; and
   a non-transitory computer-readable storage medium having stored thereon program instructions, the program instructions executable by the at least one hardware processor to:
   receive a plurality of CBCT scans, each comprising a series of axial slices, wherein said CBCT scans are associated with a cohort of subjects comprising a first subgroup of subjects having each one or more maxillofacial bone lesions, and a second subgroup of subjects having no maxillofacial bone lesions, apply a feature extraction operation to extract a set of features from said axial slices in each of said CBCT scans, at a training stage, train a machine learning model on a training dataset comprising:

(i) all of said extracted sets of features, and (ii) annotations indicating boundaries of bone lesions in said axial slices, to obtain a trained machine learning model configured to detect and segment a bone lesion in an axial slice from a CBCT scan.

2. The system of claim 1, wherein said program instructions are further executable, at an inference stage, to apply said trained machine learning model to a target CBCT scan associated with a target subject, to detect and segment a bone lesion in axial slices in said target CBCT scan.

3. The system of claim 2, wherein said program instructions are further executable to:

(i) perform pair-wise analysis with respect to successive pairs of axial slices within said target CBCT scan, to calculate a pixel-wise overlap of said segmentations in each of said successive pairs, wherein said successive pairs may be nonconsecutive pairs;

(ii) identify a subgroup comprising a minimum number of successive axial slices in which said pixel-wise overlap exceeds a specified threshold, as representing an actual bone lesion; and (iii) correct segmentation results in any of said axial slices within said subgroup in which said segmentation is incomplete, based on said segmentations in neighboring axial slices.

4. The system of claim 3, wherein said program instructions are further executable to generate a 3D segmentation of said bone lesion from said identified subgroup of axial slices.

5. The system of claim 1, wherein said feature extraction operation employs a feature pyramid network (FPN) configured to extract proportionally-sized feature maps at multiple resolution levels from an input CBCT axial slice.

6. The system of claim 1, wherein said annotations indicating said boundaries of said bone lesions comprise one of the following:

(i) an exact outline of said bone lesions, wherein said segmenting comprises an exact outline of said bone lesions, or (ii) a bounding box enclosing said bone lesions, wherein said segmenting comprises a bounding box enclosing said bone lesions.

7. The system of claim 1, wherein said training dataset further comprises annotations indicating a malignancy of said bone lesions, and wherein said trained machine learning model is further configured to a predict of a malignancy with respect to said bone lesion in said target axial slice.

8. The system of claim 1, wherein said training dataset further comprises annotations indicating a care prioritization level with respect to said one or more bone lesions, and wherein said trained machine learning model is further configured to predict said care prioritization level with respect to said bone lesion in said target axial slice.

9. A computer-implemented method comprising:

receiving a plurality of CBCT scans, each comprising a series of axial slices, wherein said CBCT scans are associated with a cohort of subjects comprising a first subgroup of subjects having each one or more maxillofacial bone lesions, and a second subgroup of subjects having no maxillofacial bone lesions;

applying a feature extraction operation to extract a set of features from said axial slices in each of said CBCT scans;

at a training stage, training a machine learning model on a training dataset comprising:

(i) all of said extracted sets of features, and (ii) annotations indicating boundaries of bone lesions in said axial slices, to obtain a trained machine learning model configured to detect and segment a bone lesion in an axial slice from a CBCT scan.

10. The computer-implemented method of claim 9, further comprising, at an inference stage, applying said trained machine learning model to a target CBCT scan associated with a target subject, to detect and segment a bone lesion in axial slices in said target CBCT scan.

11. The computer-implemented method of claim 10, further comprising:

(i) performing pair-wise analysis with respect to successive pairs of axial slices within said target CBCT scan, to calculate a pixel-wise overlap of said segmentations in each of said successive pairs, wherein said successive pairs may be nonconsecutive pairs;

(ii) identifying a subgroup comprising a minimum number of successive axial slices in which said pixel-wise overlap exceeds a specified threshold, as representing an actual bone lesion; and (iii) correcting segmentation results in any of said axial slices within said subgroup in which said segmentation is incomplete, based on said segmentations in neighboring axial slices.

12. The computer-implemented method of claim 11, further comprising generating a 3D segmentation of said bone lesion from said identified subgroup of axial slices.

13. The computer-implemented method of claim 9, wherein said feature extraction operation employs a feature pyramid network (FPN) configured to extract proportionally-sized feature maps at multiple resolution levels from an input CBCT axial slice.

14. The computer-implemented method of claim 9, wherein said annotations indicating said boundaries of said bone lesions comprise one of the following:

(i) an exact outline of said bone lesions, wherein said segmenting comprises an exact outline of said bone lesions, or (ii) a bounding box enclosing said bone lesions, wherein said segmenting comprises a bounding box enclosing said bone lesions.

15. The computer-implemented method of claim 9, wherein said training dataset further comprises annotations indicating a malignancy of said bone lesions, and wherein said trained machine learning model is further configured to a predict of a malignancy with respect to said bone lesion in said target axial slice.

16. The computer-implemented method of claim 9, wherein said training dataset further comprises annotations indicating a care prioritization level with respect to said one or more bone lesions, and wherein said trained machine learning model is further configured to predict said care prioritization level with respect to said bone lesion in said target axial slice.

17. A computer program product comprising a non-transitory computer-readable storage medium having program instructions embodied therewith, the program instructions executable by at least one hardware processor to:

receive a plurality of CBCT scans, each comprising a series of axial slices, wherein said CBCT scans are associated with a cohort of subjects comprising a first subgroup of subjects having each one or more maxillofacial bone lesions, and a second subgroup of subjects having no maxillofacial bone lesions;

apply a feature extraction operation to extract a set of features from said axial slices in each of said CBCT scans;

at a training stage, train a machine learning model on a training dataset comprising:
  (i) all of said extracted sets of features, and
  (ii) annotations indicating boundaries of bone lesions in said axial slices,
to obtain a trained machine learning model configured to detect and segment a bone lesion in an axial slice from a CBCT scan.

18. The computer-implemented method of claim 17, wherein said program instructions are further executable, at an inference stage, to apply said trained machine learning model to a target CBCT scan associated with a target subject, to detect and segment a bone lesion in axial slices in said target CBCT scan.

19. The computer-implemented method of claim 18, wherein said program instructions are further executable to:
  (i) perform pair-wise analysis with respect to successive pairs of axial slices within said target CBCT scan, to calculate a pixel-wise overlap of said segmentations in each of said successive pairs, wherein said successive pairs may be nonconsecutive pairs;
  (ii) identify a subgroup comprising a minimum number of successive axial slices in which said pixel-wise overlap exceeds a specified threshold, as representing an actual bone lesion; and
  (iii) correct segmentation results in any of said axial slices within said subgroup in which said segmentation is incomplete, based on said segmentations in neighboring axial slices.

20. The computer-implemented method of claim 19, wherein said program instructions are further executable to generate a 3D segmentation of said bone lesion from said identified subgroup of axial slices.

* * * * *